(12) United States Patent
Zhou et al.

(10) Patent No.: US 11,421,225 B2
(45) Date of Patent: Aug. 23, 2022

(54) METHODS AND SYSTEMS FOR MODULATING INTRACELLULAR GENE EXPRESSION

(71) Applicant: The Texas A&M University System, College Station, TX (US)

(72) Inventors: Yubin Zhou, Houston, TX (US); Yun Huang, Houston, TX (US); Nhung T. Nguyen, Houston, TX (US); Lian He, Houston, TX (US)

(73) Assignee: The Texas A&M University System, College Station, TX (US)

( * ) Notice: Subject to any disclaimer, the term of this patent is extended or adjusted under 35 U.S.C. 154(b) by 512 days.

(21) Appl. No.: 16/581,587

(22) Filed: Sep. 24, 2019

(65) Prior Publication Data
US 2020/0095576 A1 Mar. 26, 2020

Related U.S. Application Data

(60) Provisional application No. 62/735,968, filed on Sep. 25, 2018.

(51) Int. Cl.
| | |
|---|---|
| *C12N 15/11* | (2006.01) |
| *C12N 9/22* | (2006.01) |
| *C12N 15/90* | (2006.01) |
| *C12N 15/85* | (2006.01) |

(52) U.S. Cl.
CPC .............. *C12N 15/11* (2013.01); *C12N 9/22* (2013.01); *C12N 15/907* (2013.01); *C12N 2800/80* (2013.01)

(58) Field of Classification Search
None
See application file for complete search history.

(56) References Cited

PUBLICATIONS

Polstein et al. (Nat Chem Biol. Mar. 2015 ; 11(3): 198-200).*

* cited by examiner

*Primary Examiner* — Suzanne M Noakes
*Assistant Examiner* — Jae W Lee
(74) *Attorney, Agent, or Firm* — Winstead PC

(57) ABSTRACT

In an embodiment, a device for modulating intracellular gene expression, the device having a calcium actuator component and a transcription reprogramming component. In another embodiment, a method for modulating intracellular gene expression, where the method includes inducing a system having a calcium actuator component and a transcription reprogramming component with at least one of light and a chemical, causing an increase in $Ca^{2+}$, and translocating the transcription reprogramming component from cytosol to the nucleus. In a further embodiment, a method for modulating gene intracellular expression, where the method includes inducing a system having an NIR-stimulable optogenetic platform with at least one of light and a chemical, where the NIR-stimulable optogenetic platform facilitates $Ca^{2+}$ release and the NIR-stimulable optogenetic platform is LOV2-SOAR, causing an increase in $Ca^{2+}$, and translocating a calcium-responsive dCas9 fusion construct from cytosol to the nucleus, where the calcium-responsive dCas9 fusion construct is $NFAT_{1-460}$-dCas9-VP64.

18 Claims, 13 Drawing Sheets

Specification includes a Sequence Listing.

METHODS AND SYSTEMS FOR MODULATING INTRACELLULAR GENE EXPRESSION

CROSS-REFERENCE TO RELATED APPLICATIONS

This patent application claims priority from, and incorporates by reference the entire disclosure of, U.S. Provisional Patent Application No. 62/735,968 filed on Sep. 25, 2018.

STATEMENT REGARDING FEDERALLY SPONSORED RESEARCH

This invention was made with government support under R01GM112003, R01HL134780, and R21GM126532 awarded by National Institutes of Health. The government has certain rights in the invention.

TECHNICAL FIELD

The present disclosure relates generally to methods and systems for modulating intracellular gene expression, and more particularly, but not by way of limitation, to chemical and light-inducible transcriptional reprogramming devices and methods of use thereof.

BACKGROUND

This section provides background information to facilitate a better understanding of the various aspects of the disclosure. It should be understood that the statements in this section of this document are to be read in this light, and not as admissions of prior art.

Tools capable of modulating gene expression in living organisms are very useful for interrogating the gene regulatory network and controlling biological processes. The catalytically inactive CRISPR/Cas9 (dCas9; Cas 9 endonuclease dead; dead Cas9), when fused with repressive or activating effectors, functions as a versatile platform to reprogram gene transcription at targeted genomic loci. However, without temporal control, the application of these reprogramming tools will likely cause off-target effects and lack strict reversibility. To overcome this limitation, it is disclosed herein, the development of a transcriptional reprogramming device that is either light-inducible or chemical-inducible, which combines photoswitchable genetically encoded calcium actuators with dCas9 to control gene expression. By fusing an engineered $Ca^{2+}$-responsive NFAT (Nuclear factor of activated T-cells) fragment with dCas9 and transcriptional coactivators, the present disclosure seeks to harness the power of light to achieve photoinducible transcriptional reprogramming in mammalian cells. This synthetic system (designated CaRROT for Calcium-responsive transcriptional reprogramming tool) can also be used to document calcium-dependent activity in mammals after exposure to ligands or chemicals that would elicit calcium response inside cells.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an aspect, the present disclosure relates to a device for modulating intracellular gene expression. In some embodiments, the device includes a calcium actuator component and a transcription reprogramming component. In some embodiments, the calcium actuator component is an NIR (near-infrared light)-stimulable optogenetic platform. In some embodiments, the NIR-stimulable optogenetic platform photoactivates ORAI calcium channels to thereby induce $Ca^{2+}$ influx. In some embodiments, the NIR-stimulable optogenetic platform includes an ORAI-activating fragment from a cytoplasmic domain of at least one of STIM1 and LOV2. In some embodiments, the cytoplasmic domain of STIM1 is at least one of SOAR and CAD. In some embodiments, the NIR-stimulable optogenetic platform is LOV2-SOAR.

In some embodiments, the transcription reprogramming component is a calcium-responsive dCas9 fusion construct having an N-terminal fragment of NFAT (residues $NFAT_{1-460}$) fused with dCas9 and a transcriptional coactivator. In some embodiments, the transcriptional coactivator is at least one of VP64 and VP160. In some embodiments, the calcium-responsive dCas9 fusion construct is $NFAT_{1-460}$-dCas9-VP64. In some embodiments, the transcription reprogramming component translocates from cytosol to the nucleus upon at least one of photoactivation and chemical activation.

In some embodiments, the calcium actuator component has a sequence including, but not limited to, SEQ ID NO: 1, SEQ ID NO: 2, SEQ ID NO: 6, SEQ ID NO: 7, SEQ ID NO: 8, or SEQ ID NO: 9. In some embodiments, the transcription reprogramming component has a sequence including, but not limited to, SEQ ID NO: 3, SEQ ID NO: 4, or SEQ ID NO: 5. In some embodiments, the device includes a small guide RNA (sgRNA). In some embodiments, the sgRNA has a sequence including, without limitation, SEQ ID NO: 10, SEQ ID NO: 11, or SEQ ID NO: 12.

In another aspect, the present disclosure relates to a device for modulating intracellular gene expression. In some embodiments, the device includes (i) a calcium actuator component and (ii) a transcription reprogramming component or a gene expression reprogramming component. In some embodiments, the calcium actuator component is an NIR-stimulable optogenetic platform. In some embodiments, the NIR-stimulable optogenetic platform photoactivates ORAI calcium channels to thereby induce $Ca^{2+}$ influx. In some embodiments, the NIR-stimulable optogenetic platform includes an ORAI-activating fragment from a cytoplasmic domain of at least one of STIM1 and LOV2. In some embodiments, the cytoplasmic domain of STIM1 is at least one of SOAR and CAD. In some embodiments, the NIR-stimulable optogenetic platform is LOV2-SOAR.

In some embodiments, the transcription reprogramming component is a calcium-responsive dCas9 fusion construct having an N-terminal fragment of NFAT (residues $NFAT_{1-460}$) fused with dCas9 and a transcriptional coactivator. In some embodiments, the transcriptional coactivator is at least one of VP64 and VP160. In some embodiments, the calcium-responsive dCas9 fusion construct is $NFAT_{1-460}$-dCas9-VP64. In some embodiments, the transcription reprogramming component translocates from cytosol to the nucleus upon at least one of photoactivation and chemical activation.

In some embodiments, the gene expression reprogramming component is a fusion protein comprising (i) a calcium-responsive nuclear translocation polypeptide and (ii) a gene regulator comprising a nuclease and a transcription regulatory effector. The nuclease may exhibit reduced nucleic acid cleaving activity.

In some embodiments, the calcium actuator component has a sequence including, but not limited to, SEQ ID NO: 1, SEQ ID NO: 2, SEQ ID NO: 6, SEQ ID NO: 7, SEQ ID NO: 8, or SEQ ID NO: 9. In some embodiments, the transcription reprogramming component has a sequence including, but not limited to, SEQ ID NO: 3, SEQ ID NO: 4, or SEQ ID NO: 5. In some embodiments, the device includes a small guide RNA (sgRNA). In some embodiments, the sgRNA has a sequence including, without limitation, SEQ ID NO: 10, SEQ ID NO: 11, or SEQ ID NO: 12.

In another aspect, the present disclosure relates to a method for modulating intracellular gene expression. In some embodiments, the method includes inducing a system having a calcium actuator component and a transcription reprogramming component with at least one of light and a chemical, causing an increase in $Ca^{2+}$, and translocating the transcription reprogramming component from cytosol to the nucleus. In some embodiments, the calcium actuator component is an NIR-stimulable optogenetic platform and the NIR-stimulable optogenetic platform photoactivates ORAI calcium channels to thereby induce $Ca^{2+}$ influx. In some embodiments, the NIR-stimulable optogenetic platform includes an ORAI-activating fragment from a cytoplasmic domain of at least one of STIM1 and LOV2. In some embodiments, the cytoplasmic domain of STIM1 is at least one of SOAR and CAD. In some embodiments, the NIR-stimulable optogenetic platform is LOV2-SOAR.

In some embodiments, the transcription reprogramming component is a calcium-responsive dCas9 fusion construct having an N-terminal fragment of NFAT (residues $NFAT_{1-460}$) fused with dCas9 and a transcriptional coactivator. In some embodiments, the transcriptional coactivator is at least one of VP64 and VP160. In some embodiments, the calcium-responsive dCas9 fusion construct is $NFAT_{1-460}$-dCas9-VP64.

In another aspect, the present disclosure pertains to a method for modulating gene intracellular expression. In some embodiments, the method includes inducing a system having an NIR-stimulable optogenetic platform with at least one of light and a chemical, where the NIR-stimulable optogenetic platform facilitates $Ca^{2+}$ release, and where the NIR-stimulable optogenetic platform is LOV2-SOAR. In some embodiments, the method includes causing an increase in $Ca^{2+}$ and translocating a calcium-responsive dCas9 fusion construct from cytosol to the nucleus, where the calcium-responsive dCas9 fusion construct is $NFAT_{1-460}$-dCas9-VP64.

BRIEF DESCRIPTION OF THE DRAWINGS

A more complete understanding of the subject matter of the present disclosure may be obtained by reference to the following Detailed Description when taken in conjunction with the accompanying Drawings.

FIG. 3A shows design of dCas9-fusion constructs for inducible nuclear translocation: (i) fusion with light-sensitive NLS signals (BiNLS: V1-V2); or (ii) through $Ca^{2+}$-dependent nuclear translocation (V3-V5). FIG. 3B shows Opto-CRAC designed to photoinduce $Ca^{2+}$ influx by optimizing STIM1-CT fragments, the linker and fusion to LOV2-binder Zdk. FIG. 3C shows basal fluorescence intensities of GCaMP6s-HeLa cells transfected with indicated Opto-CRAC constructs in the dark. At least 30 cells were analyzed in the assay for each construct. FIG. 3D shows light-inducible fold-change in the GCaMP6s fluorescence intensity (at 2 min postphotostimulation at 470 nm; 50 µW/cm²) in HeLa cells expressing the indicated second generation Opto-CRAC constructs. Data were shown as mean±SD (n=30 cells from three independent experiments). FIG. 3E shows time course showing the light-inducible increase of GCaMP6s signals in HeLa cells expressing Opto-CRAC-B10. Data were shown as mean±SD (n=30 cells). FIGS. 3F-3G show time course showing the fold-change of nuclear GFP intensity following blue light stimulation, FIG. 3F, and quantification of signals before and after light illumination for 30 min, FIG. 3G. Data were shown as mean±SD (n=9). Scale bar: 5 µm. ****P<0.0001 compared to the dark group (two-tailed Student's t-test).

FIG. 4A shows a schematic of CaRROT to chemically or photoinduce EGFP reporter expression. FIG. 4B shows time course showing the changes of GFP signals in the imaging field. FIG. 4C shows quantification of EGFP reporter intensities before and after light stimulation or TG treatment. Data were showed as mean±SD (n=9). P<0.01; *P<0.001 compared to untreated conditions (two-tailed Student's t-test).

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Diverse cellular activities such as cell growth, cell differentiation, metabolism, and homeostasis are dictated by complex gene networks and active transcriptional regulation. To illuminate the gene function during these biological processes, interventional tools that would enable real time manipulation and perturbation of target gene expression are needed. The clustered regularly interspaced short palindromic repeats (CRISPR)-associated-9 nuclease also known as Cas9 derived from *Streptococcus pyogenes* has emerged recently as a powerful tool for genome engineering. Cas9 can be guided by a single guide RNA (sgRNA) to a genomic target site that is complementary to the sgRNA and wherein, the genomic target site is juxtaposed to a protospacer adjacent motif (PAM) sequence: NGG. The CRISPR-Cas9 genome editing system only requires two major molecules to bind to a target DNA sequence, and thus has a great potential to become an RNA-dependent DNA recognition platform. Lately, the engineered catalytically inactive Cas9 (or dCas9) has been developed as a robust tool for targeted endogenous gene regulation without genetically altering the DNA sequence. The dCas9-sgRNA complex can induce repression of endogenous genes in bacteria by blocking RNA polymerase or perturbing transcription factor binding. Additionally, dCas9 fused to effector domains such as multiple tandem copies of Herpes Simplex Viral Protein 16 (VP64) or p65 activator domain (p65AD) have been shown to activate reporter genes or endogenous genes both in *E. coli* and human cells. However, without temporal control, i.e., time-dependent control, the application of these reprogramming tools will likely cause off-target effects and lack strict reversibility.

Figure 1:
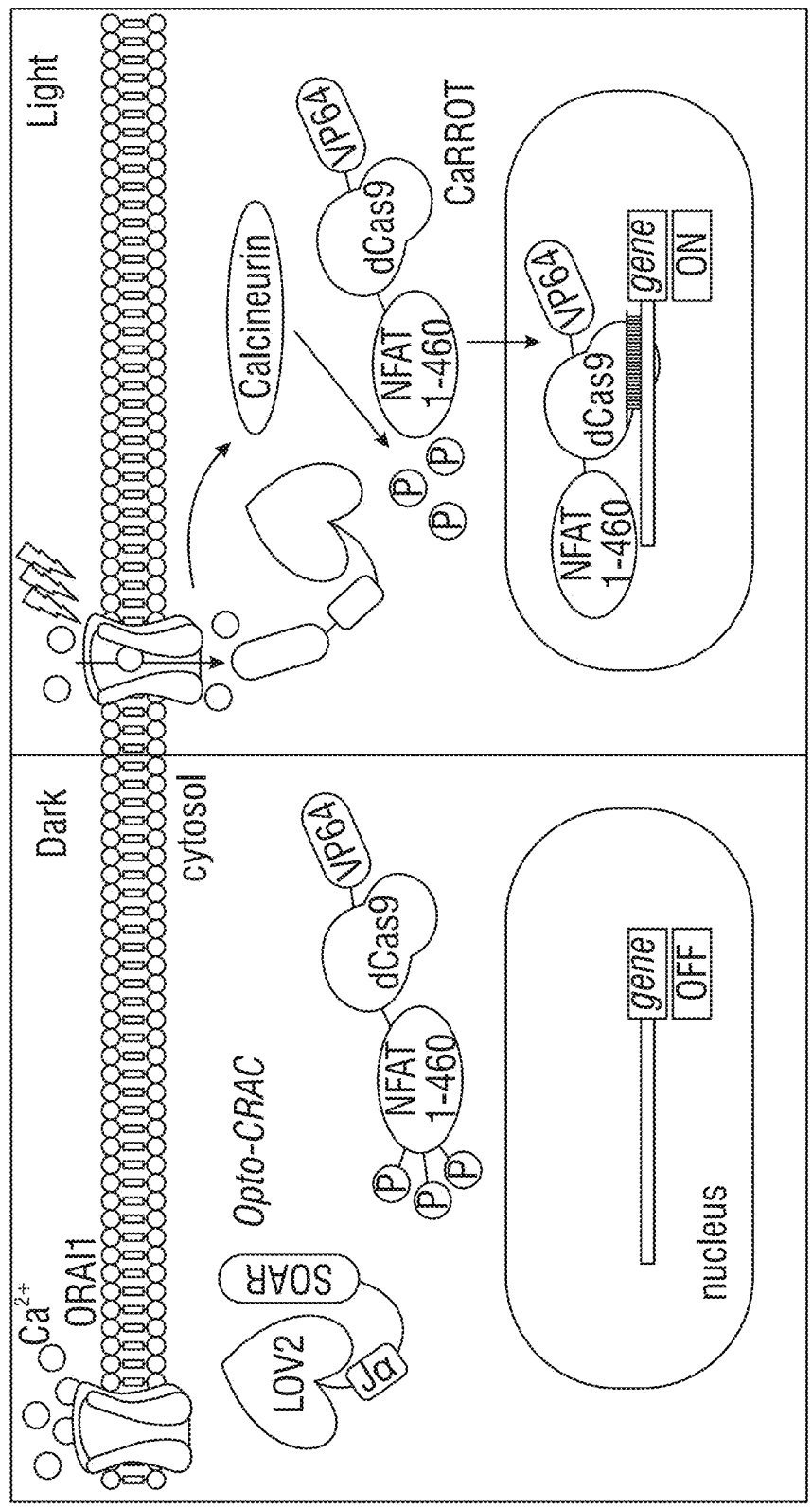
FIG. 1 illustrates a design of genetically encoded CaRROT to enable spatiotemporal control of transcriptional reprogramming in mammals. This synthetic device is composed of (i) second-generation Opto-CRAC made of LOV2-SOAR chimeras that could photoactivate ORAI calcium channels on the plasma membrane with tight control over $Ca^{2+}$ signals; and (ii) a calcium-responsive dCas9 fusion construct (e.g., $NFAT_{1-460}$-dCas9-VP64). The N-terminal NFAT fragment used in the design lacks the C-terminal DNA binding domain to avoid binding to endogenous NFAT targets. In the dark, CaRROT stays in the cytosol. Upon blue light illumination, CaRROT undergoes light-inducible nuclear translocation due to the cleavage of the phosphate groups (P) by calcineurin to turn on gene expression at targeted loci in the presence of small guide RNAs (sgRNAs). In addition to light, chemicals or ligands that could elicit intracellular calcium mobilization could likewise rewire calcium signaling to achieve inducible transcriptional reprogramming at targeted genomic loci.

In order to overcome this limitation, the present disclosure is directed to generating synthetic chemical or light-sensitive dCas9 nuclear translocation systems. This design combines genetically encoded photoactivatable Ca$^{2+}$ actuators with an engineered Ca$^{2+}$-responsive transcriptional factor and dCas9-effector fusions (FIG. 1). An effective design involves using a photoswitchable Ca$^{2+}$ actuator engineered from CRAC channel (Opto-CRAC) to remotely control calcium signals and Ca$^{2+}$-dependent nuclear translocation of engineered dCas9 fusions. The present disclosure demonstrates an improved Opto-CRAC system to reduce "leakiness" of Ca$^{2+}$ influx, or dark-state background activity. Ca$^{2+}$ influx induced by Opto-CRAC activates calcineurin, a Ca$^{2+}$-dependent phosphatase, which dephosphorylates nuclear factor of activated T cells (NFAT) and subsequently leads to NFAT nuclear translocation from the cytosol (FIG. 1). In sum, by cotransfection with the Opto-CRAC system, NFAT fragment (residues 1-460) fused with dCas9-VP64 translocate into the nucleus upon blue light illumination. Nuclear dCas9 was further directed toward its target genes by sgRNA to turn on the reporter or endogenous gene expression. The calcium signals can be generated either with calcium channel agonists or light illumination. The present disclosure demonstrates the use of this chemical and light-inducible transcriptional reprogramming device (designated as CaRROT for "calcium-responsive transcriptional reprogramming tool") to modulate gene expression with high precision.

The present disclosure is directed to the CaRROT system, which is made of NFAT fragment (residues 1-460) fused to dCas9 (catalytically inactive form of CRISPR/spCas9) and transcriptional coactivators (VP64/VP160); and opto-CRAC, which is made of LOV2 fused with *Danio rerio* STIM1 (residues 341-442) or human homologs (residues 344-486). The device of the present disclosure can use chemical signals (calcium) or light (photoactivation) to tune the expression levels of endogenous genes by adding chemicals or light to induce intracellular calcium elevation in mammalian cells.

Similar to how NFAT-fused dCas9 is shuttled to nuclei by light/chemical-inducible calcium flux, CaRROT not only photoactivates gene expression but it also photo-induces gene downregulation (when fused with transcriptional suppressor such as KRAB-Krüppel associated box) or genome editing (when using WT Cas9 or homologs). These properties of CaRROT make it possible to be utilized for light/chemical-induced transcriptional reprogramming or as a genome editing tool with high spatiotemporal precision.

In order to control gene expression, dCas9 and gene effectors have been combined into two different fused proteins. The first fusion protein includes dCas9 and a first chemical or light-induced dimerizer. The second fusion protein includes a transcription regulatory effector (activator or suppressor) (VP64 or KRAB) and a second chemical or light-induced dimerizer, that is capable of binding to the first fusion protein and ultimately, the transcriptional activator domain is recruited to the target genome locus to activate gene expression. Compared to existing methods that are only inducible by light and require a replacement of the fusion protein to become chemical inducible, the device of the present disclosure can activate gene expression by light or chemicals in a controlled manner in the same system without requiring reconstruction. Additionally, the CaRROT system does not work in the dark, and therefore, would sustain a low background level, in comparison to other systems, in which dCas9 is located in the nucleus prior to switching on the light, which causes off-target effects or pre-activation.

In some embodiments, the device of the present disclosure can comprise (i) any of the subject calcium actuator (e.g., Opto-CRAC) and (ii) any of the subject transcriptional reprogramming device (e.g., CaRROT) or a gene expression reprogramming component that is inducible by light to modulate gene expression. The gene expression reprogramming component can be a fusion protein. The fusion protein can comprise a calcium-responsive nuclear translocation polypeptide, such as, for example, the NFAT fragment or derivative thereof. The fusion protein can comprise a gene regulator comprising a nuclease. In some cases, the nuclease may be mutated such that the engineered nuclease exhibits reduced (e.g., substantially reduced or deactivated) nucleic acid cleaving activity. The gene regulator can further comprise any subject transcription regulatory effector (e.g., activator or suppressor).

Examples of the nuclease can include, but are not limited to, CRISPR-associated (Cas) proteins or Cas nucleases including type I CRISPR-associated (Cas) polypeptides, type II CRISPR-associated (Cas) polypeptides (e.g., Cas9), type III CRISPR-associated (Cas) polypeptides, type IV CRISPR-associated (Cas) polypeptides, type V CRISPR-associated (Cas) polypeptides (e.g., Cpf1/Cas12a, C2c1, or c2c3), and type VI CRISPR-associated (Cas) polypeptides (e.g., C2c2/Cas13a, Cas13b, Cas13c, Cas13d); zinc finger nucleases (ZFN); transcription activator-like effector nucleases (TALEN); meganucleases; RNA-binding proteins (RBP); CRISPR-associated RNA binding proteins; recombinases; flippases; transposases; Argonaute (Ago) proteins (e.g., prokaryotic Argonaute (pAgo), archaeal Argonaute (aAgo), and eukaryotic Argonaute (eAgo)); any derivative thereof; any variant thereof; and any fragment thereof.

Upon activation by light, the gene expression reprogramming can be recruited to a target genome locus of a cell to modulate gene expression. The target genome locus may encode a molecule such as, for example, A2AR, B7.1, B7-H3/CD276, B7-H4/B7S1/B7x/Vtcn1, B7-H6, BTLA/CD272, CCR4, CD122, 4-1BB/CD137, CD27, CD28, CD40, CD47, CD70, CISH, CTLA-4/CD152, DR3, GITR, ICOS/CD278, IDO, KIR, LAG-3, OX40/CD134, PD-1/CD279, PD2, PD-L1, PD-L2, TIM-3, and VISTA/Diesl/Gi24/PD-1H (C10orf54).

WORKING EXAMPLES

Reference will now be made to specific exemplary embodiments of the present disclosure and data that provide support for such embodiments. However, it should be noted that the disclosure below is for illustrative purposes only and is not intended to limit the scope of the claimed subject matter in any way.

Table 1, shown below, illustrates sequences corresponding to cDNA sequences for Opto-CRAC and CaRROT constructs of the present disclosure. Additionally, Table 1 further illustrates Second Generation Opto-CRAC constructs and sgRNA sequences for targeting ASCL1 in accordance with the present disclosure.

TABLE 1

| cDNA Sequences for Opto-CRAC and CaRROT Constructs | |
|---|---|
| Light Sensitive NLS, Version 1 dCas9-VP64-mCh-linker-AsLOV2-NLS1 | SEQ ID NO: 1 |
| Light Sensitive NLS, Version 2 AsLov2-NLS2 | SEQ ID NO: 2 |
| CaRROT Constructs, Version 3 NLS-dCas9-VP64-mNFAT1(1-460)-GFP | SEQ ID NO: 3 |
| CaRROT Constructs, Version 4 mNFAT1(1-460)-GFP-HA-NLS-dCas9-NLS-VP64 | SEQ ID NO: 4 |
| CaRROT Constructs, Version 5 mNFAT1(1-460)-GFP-HA-dCas9-VP64 | SEQ ID NO: 5 |

| Second Generation Opto-CRAC Constructs | |
|---|---|
| LOV2-STIM1 (336-486) | SEQ ID NO: 6 |
| STIM1 (336-442) | SEQ ID NO: 7 |
| DrSTIM1 (341-442) | SEQ ID NO: 8 |
| STIM1 (347-448) | SEQ ID NO: 9 |

TABLE 1-continued

| sgRNA Sequences for Targeting ASCL1 | |
|---|---|
| ASCL1-sgRNA1 | SEQ ID NO: 10 |
| ASCL1-sgRNA2 | SEQ ID NO: 11 |
| ASCL1-sgRNA3 | SEQ ID NO: 12 |

Opto-CRAC vectors were designed by amplifying *Homo sapiens* STIM1-CT fragments (residues 336-486, 336-442, 347-448) and *Danio rerio* STIM1(341-442) using the KOD Hot start DNA polymerase (EMD Millipore, Billerica, Mass., USA) and inserted downstream of LOV2$_{404-546}$ between the HindIII-XhoI restriction sites to replace Rac1 in the pTriEX-mCherry-PARac1 plasmid (Addgene, #22027). The linker 1 (GSGLEGSGG) or linker 2 (GSGLESG) was introduced to the Opto-CRAC vectors at NotI-XhoI sites. cDNAs encoding Zdk1 and Zdk2 were obtained from the University of North Carolina at Chapel Hill. They were amplified and inserted between XhoI-XbaI sites.

To construct dCas9-based nuclear translocation vectors, NFAT (1-460) and dCas9, VP64 (derived from Addgene plasmid 22027), and GFP or BFP were introduced sequentially to AflII/AgeI/HindIII and XhoI sites of pcDNA3.1(+). The NLS oligonucleotides were also inserted during amplification depending on the construct. AsLOV2-based bipartite NLS1 and NLS2 generated from biLINUS 9 and biLINUS 11, respectively, were obtained from the University of Heidelberg, Germany. All the restriction enzymes used in the present disclosure were purchased from New England Biolabs.

The sgRNA targeting EGFP reporter, MYOD1 sgRNA 1, and sgRNA 2 were obtained from Addgene (#60719, #64137 and #64138). The sgRNAs targeting ASCL1 were generated by annealed oligo cloning using the BsmBI site of Lenti-Guide-Puro, (Addgene: #52963). EGFP reporter containing eight copies of a gRNA binding site for light-inducible dCas9 activation was obtained from Addgene (#60718).

HEK293T and HeLa cells from the American Type Culture Collection (ATCC) were maintained in DMEM medium (Gibco) supplemented with 10% FBS, 100 unit/ml penicillin and 100 µg/mL Streptomycin (Gibco) at 37° C. in a humidified atmosphere under 5% $CO_2$. For confocal imaging, $2\times10^5$ cultured cells were seeded on 35 mm glass-bottom dishes 24 h before transfection using Lipofectamine 3000 (Life Technologies) according to the manufacturer's instructions.

For measurements of $Ca^{2+}$ influx using the green color calcium indicator GCaMP6s or red indicator jRCaMP1b, 100 ng of each Opto-CRAC construct and 100 ng cytosolic GCaMP6s or jRCaMP1b were cotransfected into HeLa cells using Lipofectamine 3000. 24 h after transfection, a 488 nm laser was used to excite GFP, and a 561 nm laser to excite mCherry at intervals of 1-5 s. mCherry-positive cells were used for statistical analysis.

In order to evaluate the nuclear translocation of dCas9 variants, single dCas9-VP64-mCherry-AsLOV2-bipartite NLS Version 1.0 or Version 2.0 were transfected into Hela cells or cotransfected Opto-CRAC with one of the following constructs: CaRROT-V3, V4, and V5 then incubated for 1 day. Photostimulation was used to induce $Ca^{2+}$ influx mediated by Opto-CRAC constructs, and the cells were time-lapse recorded for more than 30 min at intervals of 2 min. Nine mCherry-positive cells (the first two constructs) and both mCherry and BFP/GFP-positive cells (the last three constructs) were selected to calculate the ratio of fluorescence signal between nuclei and the total fluorescence (nuclei plus cytosolic intensities).

Hela cells were seeded in two 6-well plates transfected with the combination of vectors in each well: BFP-tagged-CaRROT-V5 (750 ng), sgRNA (250 ng), EGFP reporter (500 ng), Opto-CRAC (250 ng). After 24 h of transfection, one plate was kept in the dark, and another plate was added TG (2 µM) or subjected to blue light irradiation (470 nm, tunable intensity of 0-50 µW/mm$^2$) for 1 h, followed by pulsed stimulation (5 s ON for every 20 s) for another 24 h to maintain the constant activation of the light-inducible system. Next, the cells were washed, trypsinized and washed with PBS twice. The levels of fluorescence protein were determined using the LSRII flow cytometer (BD Biosciences). Cells were sampled at a medium flow rate, and 10,000 cells were counted for each condition. FlowJo software (TreeStar) was used to analyze the data (EGFP$^+$ in BFP$^+$ or BFP$^+$mch$^+$ cell populations). The experiments were conducted in duplicate.

HEK293T cells were plated at approximately 5×10$^4$ cells/well in 12-well plates (Corning Inc., USA) and cultured for 24 h. Each well was transfected with 250 ng, 250 ng and 750 ng of the sgRNA expression plasmid, Opto-CRAC, and BFP-tagged-CaRROT-V5, respectively. As a positive control, plasmid encoding dCas9-NLS-VP64 and sgRNA were transfected at a 3:1 ratio. After 24 h of transfection, samples underwent blue light stimulation or incubated in the dark as described above. On the next day, mRNA was extracted using Qiagen RNeasy spin prep columns and reverse transcription PCR was performed using amfiRivert cDNA Synthesis Platinum Master Mix (genDEPOT). Relative levels of cDNA were detected using amfiSure qGreen Q-PCR Master Mix (genDEPOT) and Mastercycle Real-Time PCR (Eppendorf, USA). The data were normalized to GAPDH levels and cells transfected with an empty plasmid (control) using the ΔΔCt method.

Figure 3A:
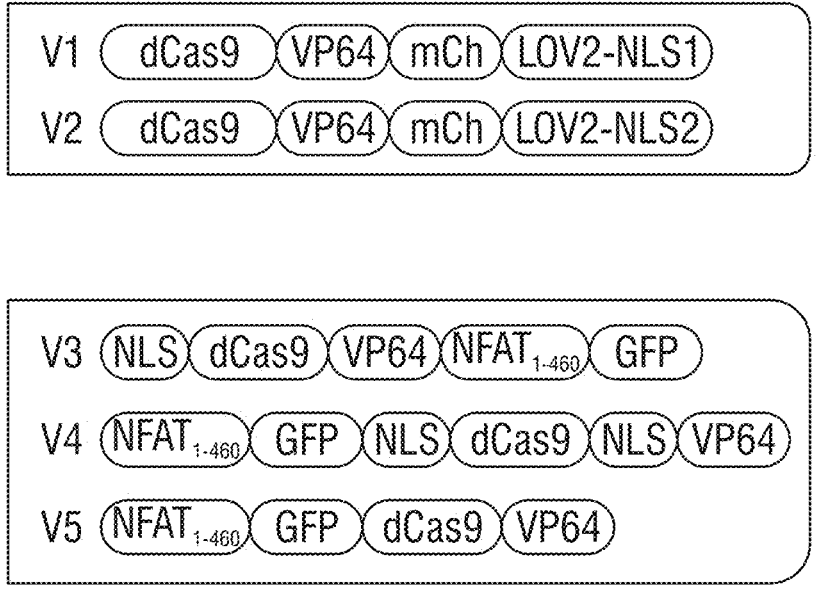
FIG. 3A, FIG. 3B, FIG. 3C, FIG. 3D, FIG. 3E, FIG. 3F and FIG. 3G illustrate the design and optimization of CaRROT and second-generation Opto-CRAC constructs to enable tight control of dCas9 nuclear translocation.

In order to regulate specific gene expression, dCas9 is required to locate in the nuclei and is directed by a sgRNA to the promoter of the targeted genes. In most applications, the nuclear localization of dCas9 is enabled by adding several nuclear localization signals (NLS) at both N and C-termini of dCas9. Without the NLS signals, dCas9 largely resides in the cytoplasm given its relatively large size and lack of a strong NLS by itself. To enable light-controllable nuclear translocation to execute its function, several photosensitive dCas9-VP64 systems were designed and constructed based on two strategies: (i) fusion of dCas9-VP64 with light-sensitive NLS; or (ii) design of a synthetic Ca$^{2+}$-dependent nuclear translocation device, thereafter termed as calcium-responsive transcriptional reprogramming tool (or CaRROT) (FIG. 3A).

For the first approach, light-sensitive NLS is designed by fusing bipartite NLS peptides to LOV2 (AsLOV2) derived from *Avena sativa* phototropin. Bipartite NLS was introduced to the C-terminal Jα helix of the AsLOV2 domain, while dCas9-VP64 was placed at the N-terminus. In the dark, NLS is caged by LOV2 domain and thus shielded from the nuclear import cargo; therefore, the fusion protein is trapped in the cytoplasm. Upon blue light illumination, photoexcitation creates a covalent adduct between LOV2 residue C450 and the cofactor FMN, allowing the undocking of the Jα helix to expose NLS. The NLS binds to importin, which mediates interactions with the nuclear pore complex, thereby causing the translocation of dCas9-VP64 from cytosol to the nuclei.

The second photoactivatable nuclear translocation approach is based on a Ca$^{2+}$-dependent system, and includes two components: (i) a GFP (green fluorescent protein)-tagged fusion protein contains dCas9, VP64 and an N-terminal fragment of NFAT (residues 1-460 without the DNA binding domain to avoid binding to endogenous NFAT targets), in which NFAT$_{1-460}$ was fused to either the N- or C-terminus of dCas9, and NLS was inserted in different positions depending on the constructs; and (ii) Opto-CRAC, which includes an ORAI-activating fragment from the cytoplasmic domain of STIM1 (SOAR or CAD) and LOV2 domain to induce Ca$^{2+}$ influx by blue light. In the dark, the SOAR/CAD domain was caged by LOV2 to prevent the activation of ORAI calcium channels. Following blue light exposure, the unwinding of the LOV2-Jα helix promoted the exposure of SOAR/CAD, which subsequently moved toward the plasma membrane to directly engage and activate ORAI1 Ca$^{2+}$ channels.

Figure 2A:
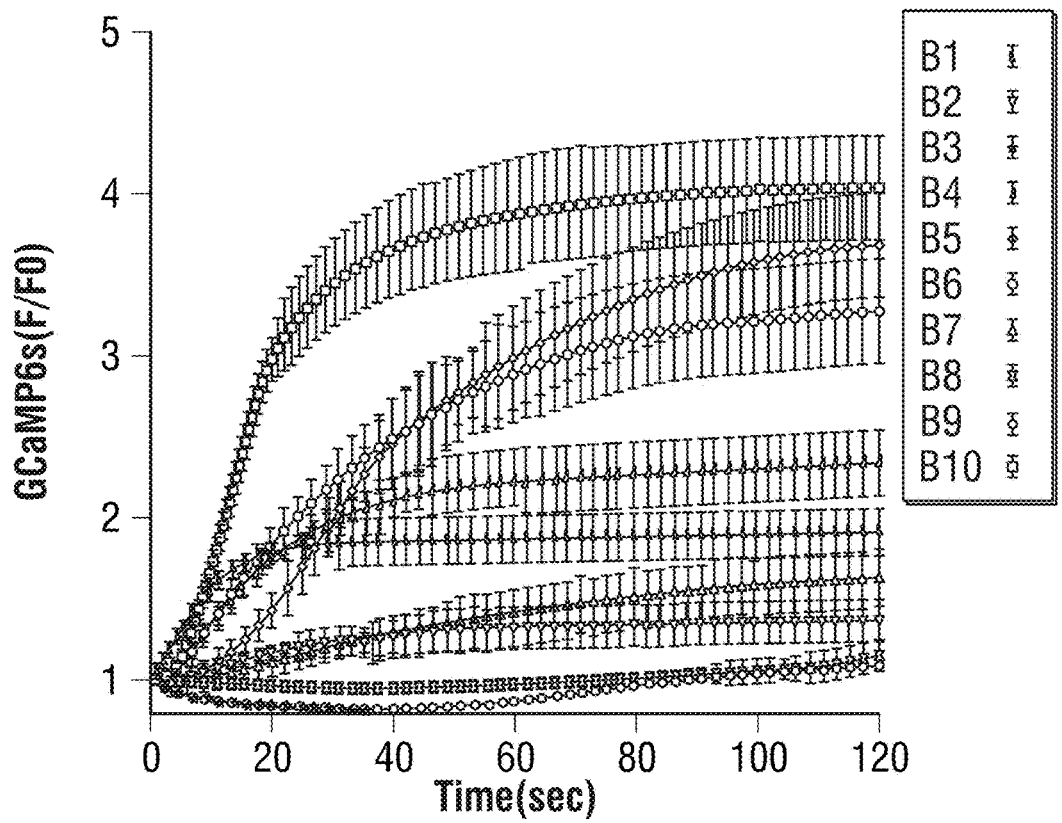
FIG. 2A illustrates time course of fluorescence changes in HeLa cells co-expressing the genetically-encoded $Ca^{2+}$ sensors (GCaMP6s) and the indicated Opto-CRAC constructs following blue light stimulation (470 nm; power density=50 µW/cm2).
Figure 2B:
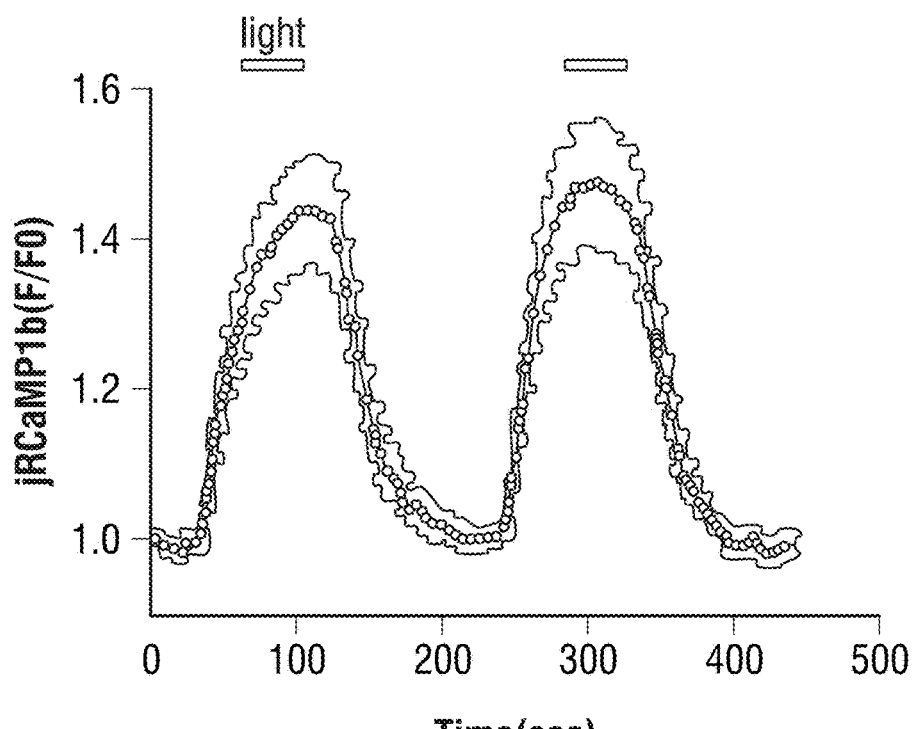
FIG. 2B illustrates monitoring Opto-CRAC-B10 induced reversible calcium influx in HeLa cells with jR-CaMP1b ($t_{1/2}$, on=18.7±1.4 sec; $t_{1/2}$, off=24.5±1.1 sec). Top bar: light stimulation at 470 nm.
Figure 3B:
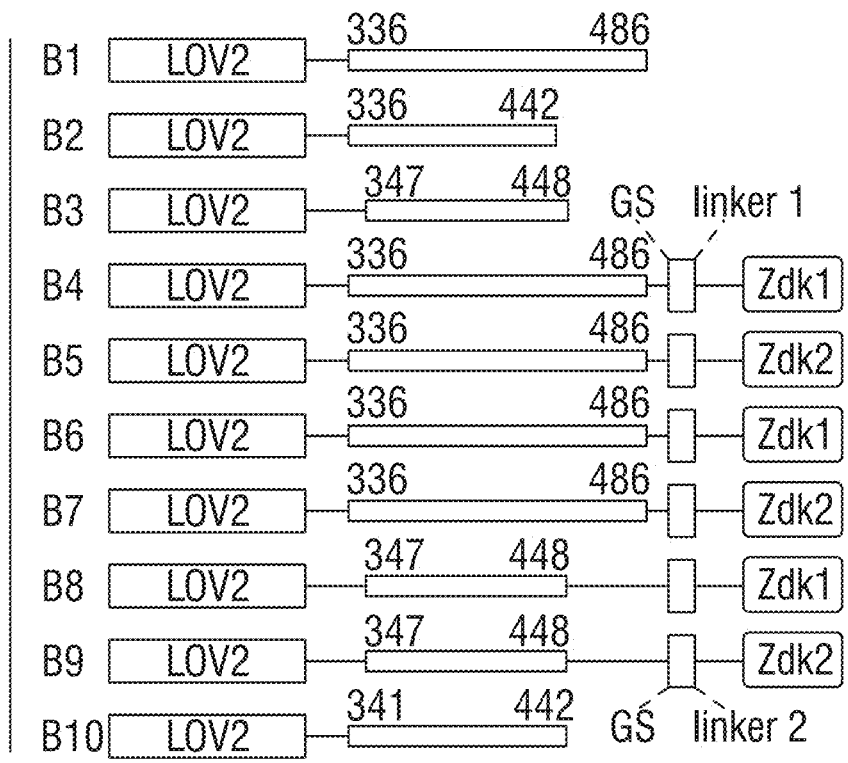
Figure 3C:
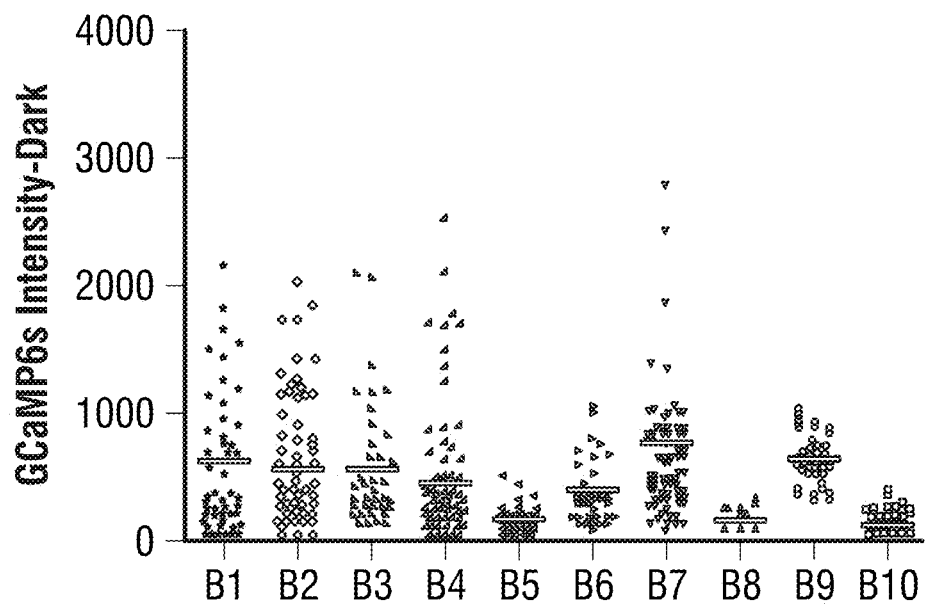
Figure 3D:
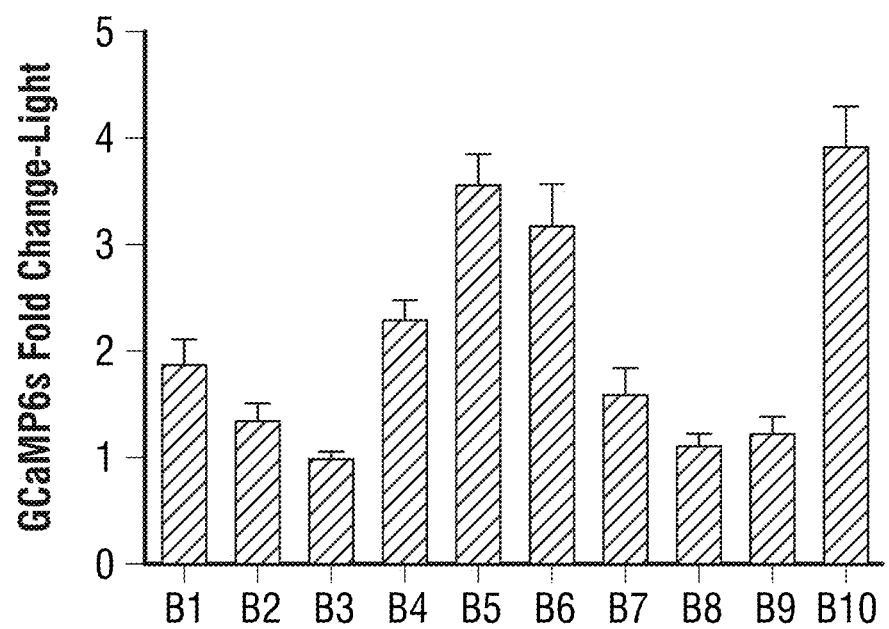
Figure 3E:
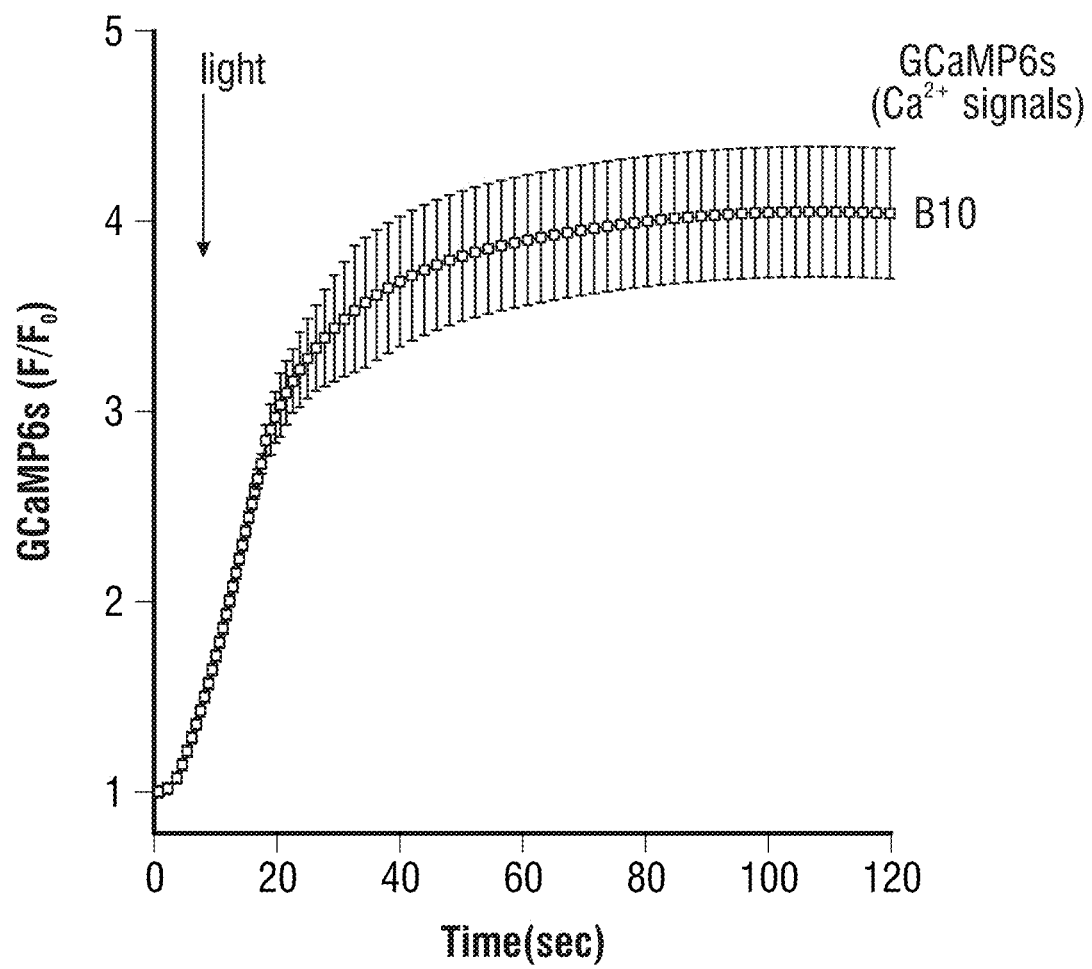

The prototypical design of Opto-CRAC contains LOV2 and a STIM1 cytosolic fragment (aa 336-486). However, this construct showed measurable dark activity (construct B1, FIG. 3B, FIG. 3C), which might cause the constitutive nuclear translocation of NFAT in the dark. To confer tighter control over the CaRROT system, a series of second-generation Opto-CRAC constructs were created by (i) varying the length of STIM1-CT fragments (B1-3; FIG. 3B); (ii) fusion to Zdark (Zdk) protein, a light-dependent LOV2 binder and changing the linkers (B4-9); or (iii) using SOAR domain derived from other species (such as zebrafish; B10). After transfecting Opto-CRAC constructs to GCaMP6s-stable HeLa cells, the best performing construct was next identified based on two criteria: (i) reduced dark activity; and (ii) enhanced dynamic ranges of calcium signal changes in response to light stimulation. Since Zdk binds to LOV2 tightly in the dark but dissociates from LOV2 upon light stimulation, it was reasoned that Zdk might serve as an additional "lock" to further cage LOV2-SOAR fusion in a quiescent configuration, thus reducing the background activation. Some of the Zdk constructs showed substantially reduced dark activity (constructs B5, B6, and B8; FIG. 3C). However, in some constructs, the addition of Zdk led to narrower dynamic ranges (B8 and B9, FIG. 3D) and slower onset of light-inducible Ca$^{2+}$ responses when compared to B1 (FIG. 2A, Table 2). Ultimately, the chimera made of LOV2 and *D. rerio* SOAR (DrSOAR; residues 341-442) turned out to be an ideal candidate with negligible dark activation but potent photoinduced calcium influx, with the activation and deactivation half-lives of 18.7 and 24.5 s, respectively (construct B10; FIG. 3D, FIG. 3E and FIG. 2B). This construct was therefore used for the downstream applications.

Table 2, shown below, illustrates a summary of the activation kinetics (activation half-lives based on representative curves shown in FIG. 2A; $t_{1/2}$, ON) of the 10 tested Opto-CRAC constructs.

TABLE 2

| Constructs | $T_{1/2, ON}$ (sec) |
|---|---|
| B1 | 6.578 |
| B2 | 18.97 |
| B3 | N/A |
| B4 | 15.7 |
| B5 | 39.77 |
| B6 | 27.42 |
| B7 | 59.51 |
| B8 | >100 |
| B9 | >100 |
| B10 | 18.7 |

Figure 3F:
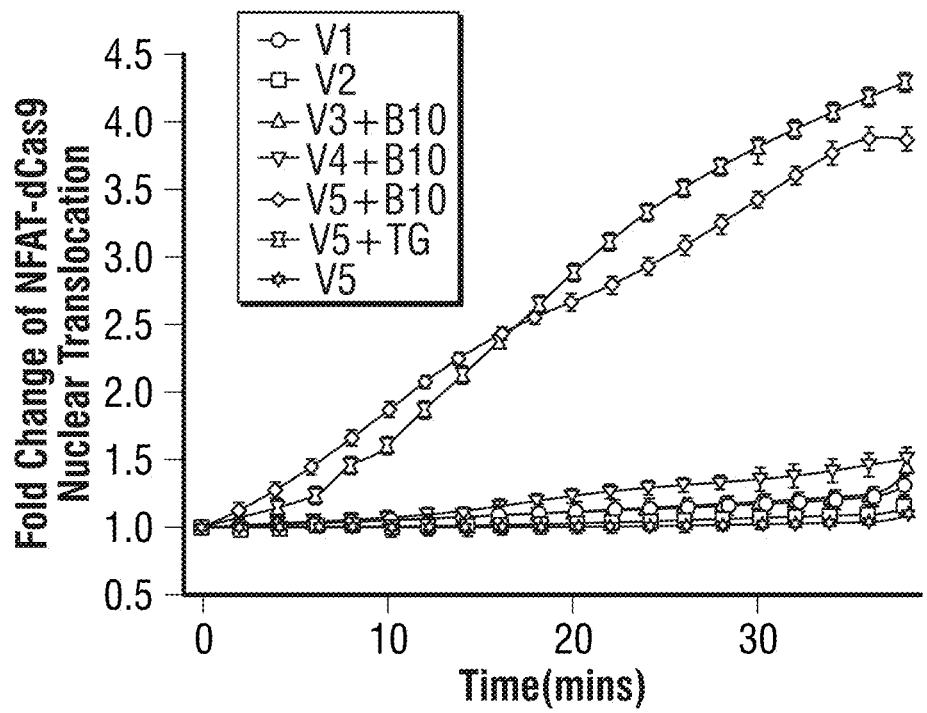
Figure 3G:
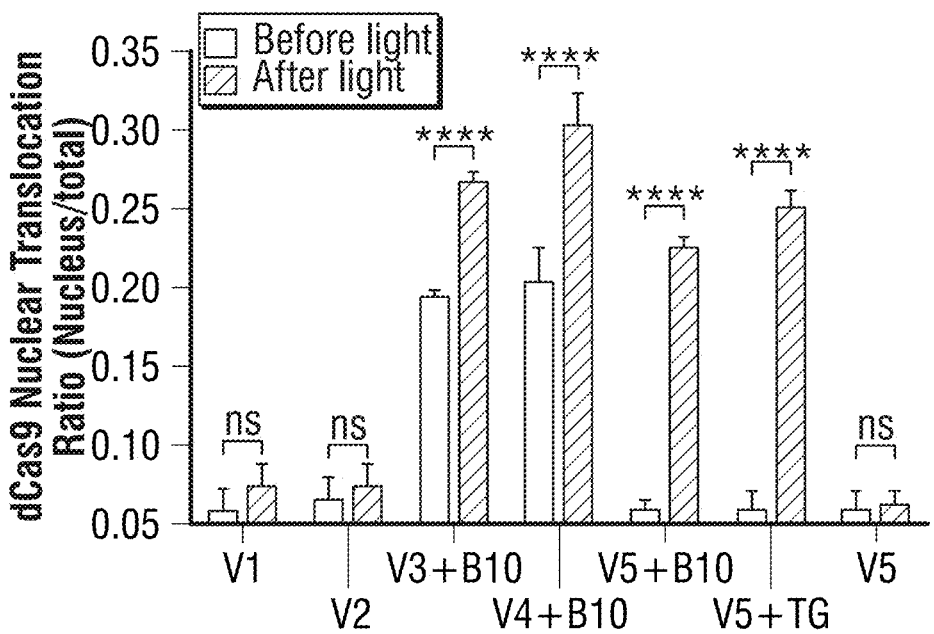

The dCas9 nuclear translocation of different designs upon blue light illumination was evaluated by transfecting HeLa cells with mCherry-tagged dCas9-VP64-LOV2-NLS constructs (FIG. 3A, constructs V1 and V2) or cotransfecting LOV2-DrSOAR (construct B10) with various CaRROT constructs (FIG. 3A, constructs V3-5). In cells expressing mCherry-tagged V1 or V2, dCas9 underwent very low translocation from cytosol to nuclei in response to blue light illumination (ns=not significant), suggesting that either the NLS is not strong enough or not fully exposed to drive nuclear import of dCas9. In contrast, for cells transfected with V3 or V4, dCas9 was observed in the nuclei prior to light illumination when cotransfected with Opto-CRAC-B10. The result indicated that NLS inserted in these constructs have a strong affinity for the import machinery, and thus shuttles the fusion protein into nuclei even in the dark. After removing all the NLS in dCas9, the CaRROT construct V5 remained exclusively in the cytosol in the dark. Upon light stimulation, CaRROT-V5 showed light-inducible translocation into the nuclei of cells cotransfected with Opto-CRAC-B10 (~3.5-fold change; FIG. 3F). This system also showed no discernible dark-state background activity (FIG. 3G), which was consistent with the minimal $Ca^{2+}$ influx "leakiness" of the improved Opto-CRAC system (FIG. 3C).

To confirm that the system could be likewise manipulated by chemicals that could alter intracellular calcium signals, thapsigargin (TG), which block the sarcoplasmic/endoplasmic reticulum $Ca^{2+}$ ATPase (SERCA) pump was used to passively induce calcium store depletion in the ER. This process is immediately followed by the activation of STIM1 to open ORAI calcium channels and cause bulky flooding of calcium ions into the cytosol. Time-lapse imaging showed that TG, similar to photoactivated Opto-CRAC, could lead to the nuclear entry of dCas9 (~4-fold changes in nuclear fluorescence signals; FIG. 3F). Taken together, these results establish that both chemical and light could be used to control the cytosol-to-nucleus shuttling of dCas9-fused transcriptional effector, which can be an indispensable step for the fusion protein to execute its function within the nuclei.

Figure 4A:
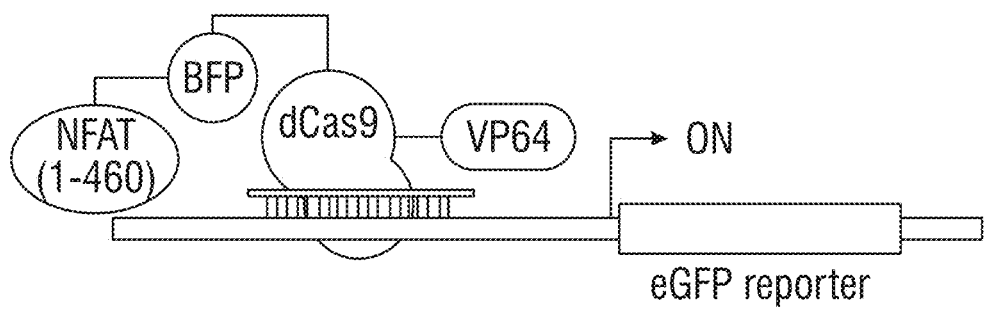
FIG. 4A, FIG. 4B and FIG. 4C illustrate the use of CaRROT to chemically or photoinduce EGFP reporter expression.
Figure 5A:
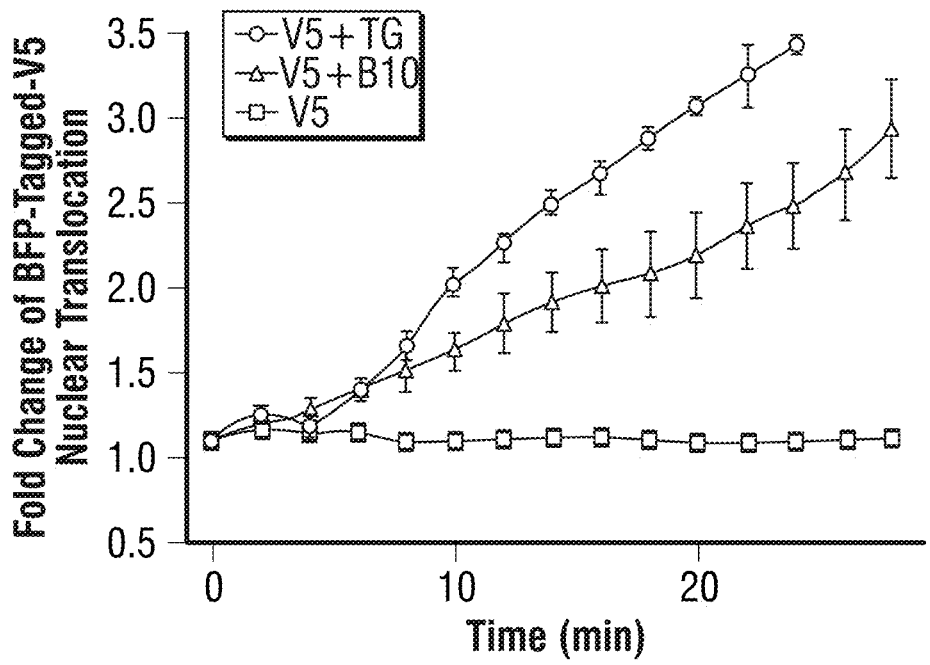
FIG. 5A and FIG. 5B illustrate time course showing the fold-change of nuclear BFP intensity following blue light stimulation, FIG. 5A, and quantification of signals before and after light illumination for 30 min, FIG. 5B. Data were shown as mean±S.D. (n=9). Scale bar: 5 µm. ***P<0.001 compared to the dark group (two-tailed Student's t-test).
Figure 5B:
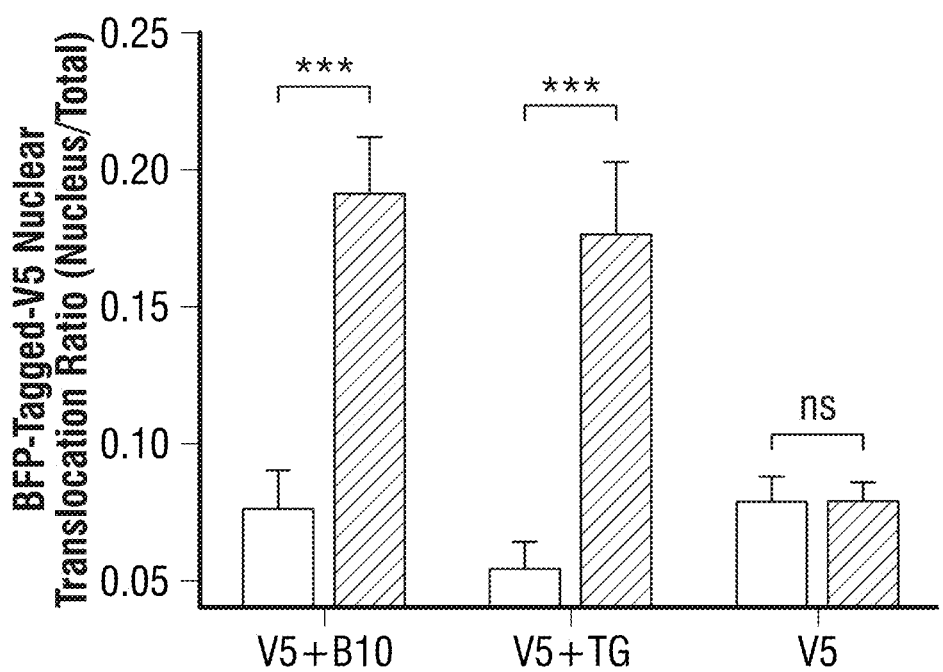

Several previous studies have demonstrated that gene activation could be achieved by targeting VP64 effector domain to the transcribed region of a gene due to its ability to recruit basal transcriptional machinery. In the design of the present disclosure, the dCas9-sgRNA complex serves as a locus-positioning apparatus to direct VP64 to targeted genomic loci, e.g., promoters of targeted genes (FIG. 4A). To rapidly evaluate if the CaRROT system can precisely control gene expression in response to light or chemicals, an EGFP reporter assay was used, in which eight repeats of a guide RNA target sequence situated upstream of a minimal cytomegalovirus (CMV) promoter. Since the activated reporter expresses EGFP, the GFP module on the CaRROT-V5 construct was replaced by BFP to avoid fluorescence overlap. Similar to GFP-tagged version, BFP-tagged CaRROT-V5 showed undetectable dark-state background activity, but underwent nuclear translocation when cotransfected with Opto-CRAC-B10 upon blue light stimulation or TG treatment (FIG. 5A-FIG. 5B). After addition of TG to induce calcium influx in cells transfected with BFP-tagged CaRROT-V5 and corresponding sgRNA, a pronounced increase in EGFP levels was observed compared with control cells without TG administration per different microscopic fields. A similar experiment was performed by using Opto-CRACV5, rather than TG, to elicit calcium entry, and noticed a similar increase of EGFP expression. As a control, cells transfected with CaRROT-V5 and sgRNA did not show the significant increase of EGFP signals regardless of the presence of light.

Figure 4B:
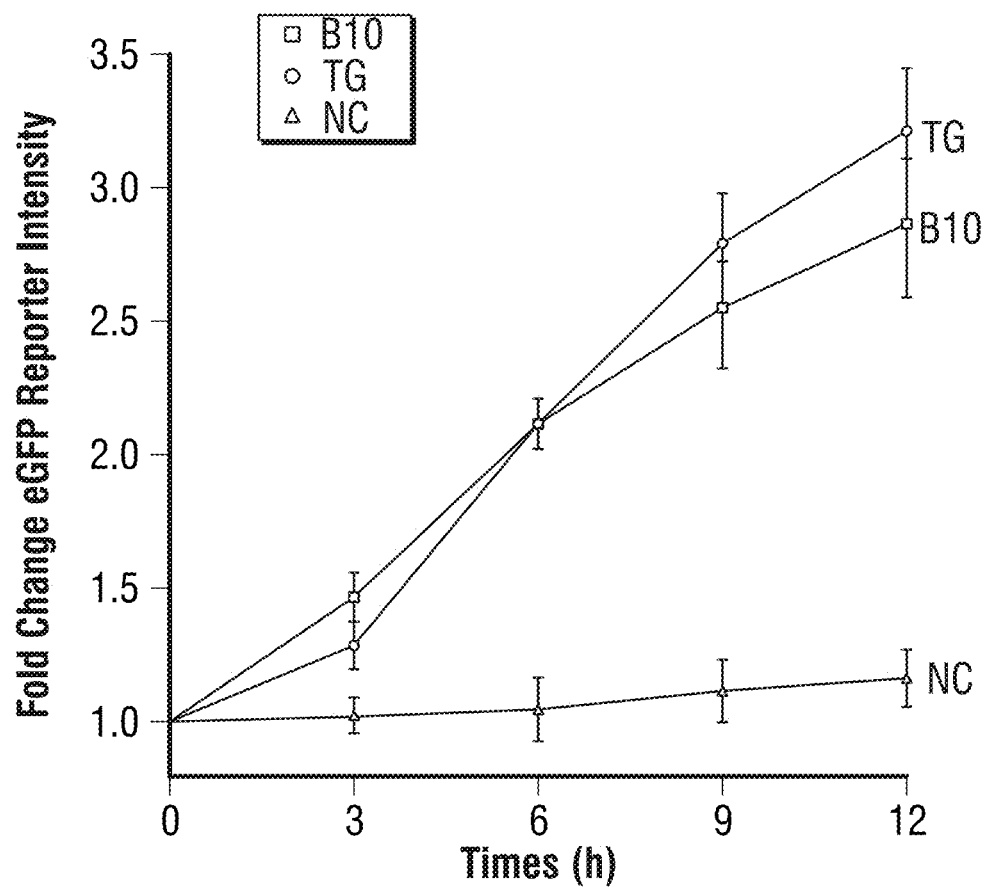
Figure 4C:
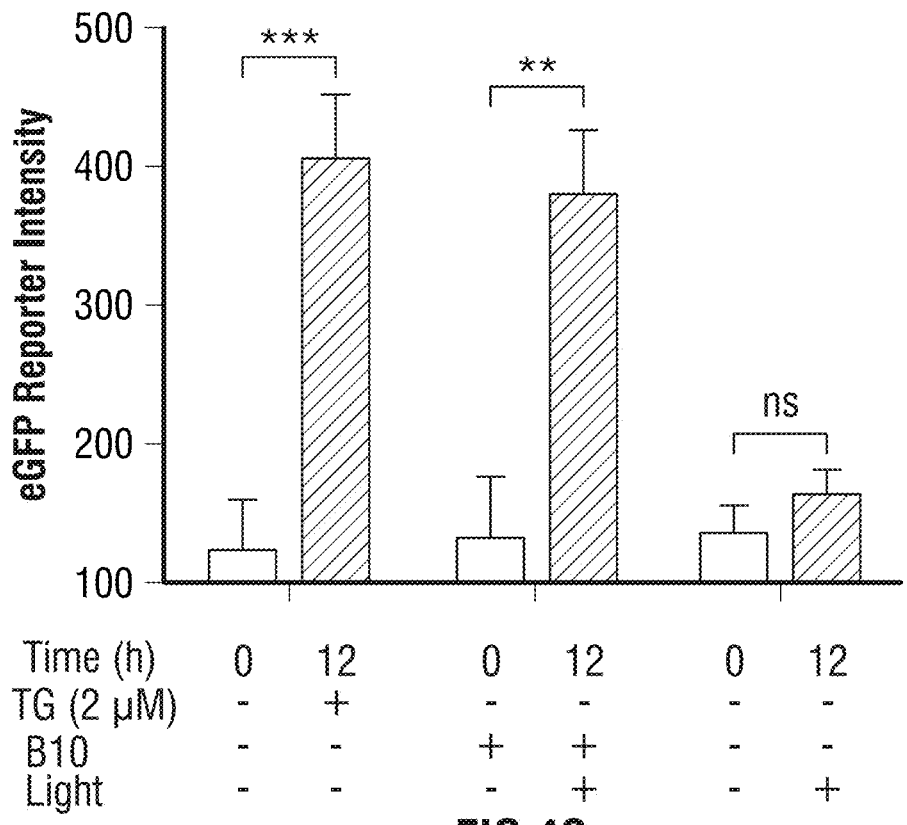

To better visualize the behaviors in the same transfected cells at real time in response to blue light, different sets of vectors were cotransfected for 24 h into Hela cells, and then recorded the time-lapse imaging with pulsed photostimulation (blue LED at 470 nm; power density of 0-50 µW/mm$^2$; 5 s ON, 20 s OFF) or by adding TG to the cells (12 h). The assay was performed with the following three groups: (i) BFP-tagged CaRROT-V5, sgRNA, Opto-CRAC-B10 and EGFP reporter; (ii) BFP-tagged CaRROT-V5, sgRNA, adding TG and EGFP reporter; (iii) BFP-tagged CaRROT-V5, sgRNA and EGFP reporter as a negative control. The addition of TG to CaRROT-V5-contained cells turned on the EGFP signals statistically higher than cells that only received CaRROT-V5 and the reporter construct. The similar trend was observed in the group of cells transfected with CaRROT-V5 and Opto-CRAC-B10, in which the EGFP signals in the same cells were markedly higher than before light stimulation and the negative control. The EGFP signals raised up to 3-fold compared to the starting point (FIG. 4B).

Figure 6A:
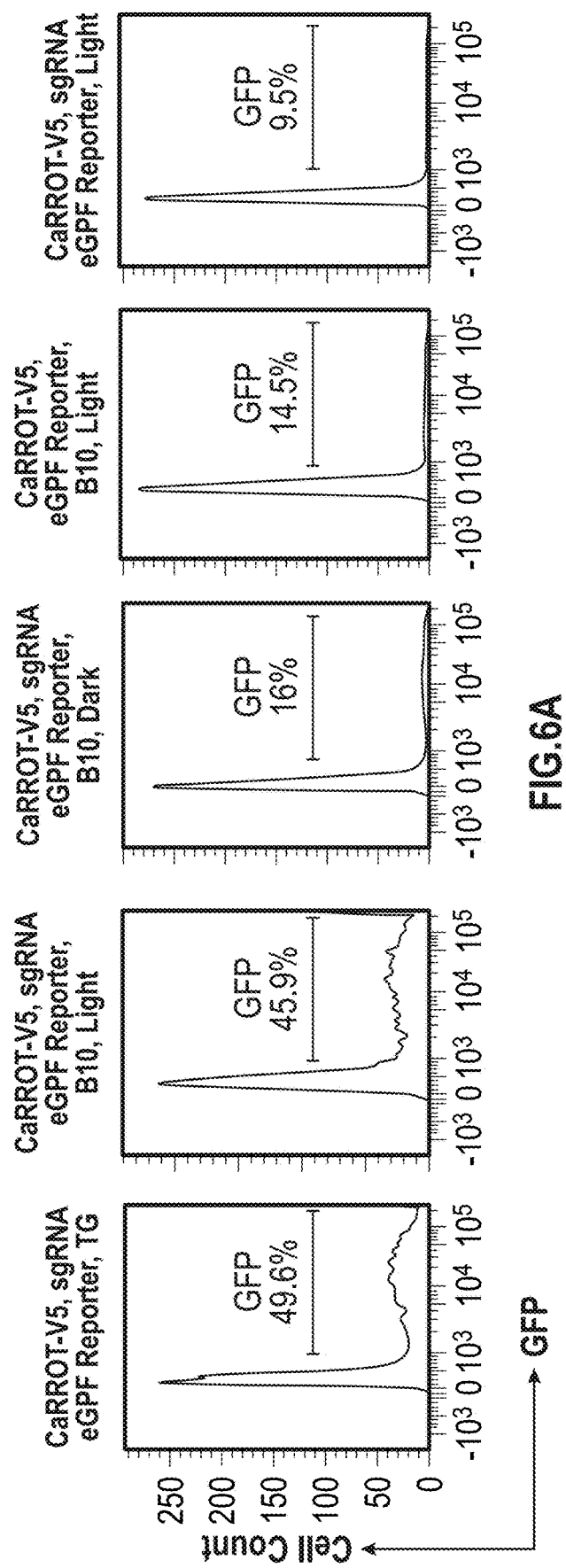
FIG. 6A and FIG. 6B illustrate the number of EGFP-positive cells was counted by flow cytometry (shown were representative data from one experiment, n=2).
Figure 6B:
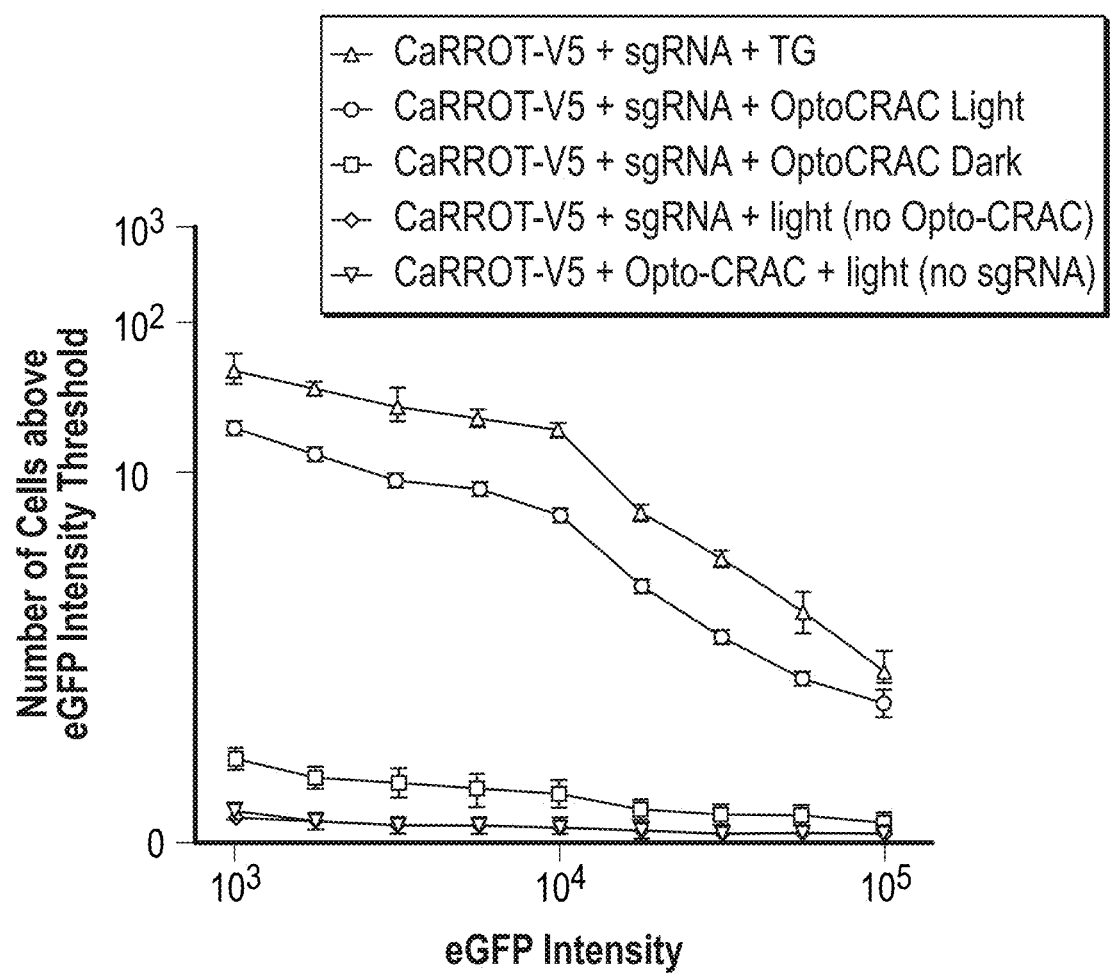

Each cell received a different amount of vectors mixture; therefore, the evaluation of the EGFP intensity of the whole cell population would better reflect the efficiency of the CaRROT system. Flow cytometry was then used to quantify the numbers of cells showing chemical or light-inducible activation of the EGFP reporter (FIG. 6A). Since the magnitude of the difference between cells irradiated with light and incubated in the dark varied on the threshold applied to the EGFP fluorescence intensity, the number of EGFP-positive cells was calculated at different indicated thresholds. The cells transfected with CaRROT-V5, Opto-CRAC-B10, sgRNA, and EGFP reporter and subjected to light illumination showed a statistically higher number of EGFP cells than either cell shielded in the dark or the negative control group at any thresholds (FIG. 6B). The similar trend was also observed in the group received CaRROT-V5 and TG, which showed significant enrichment of EGFP cells compared to negative controls (FIG. 6B).

Figure 7A:
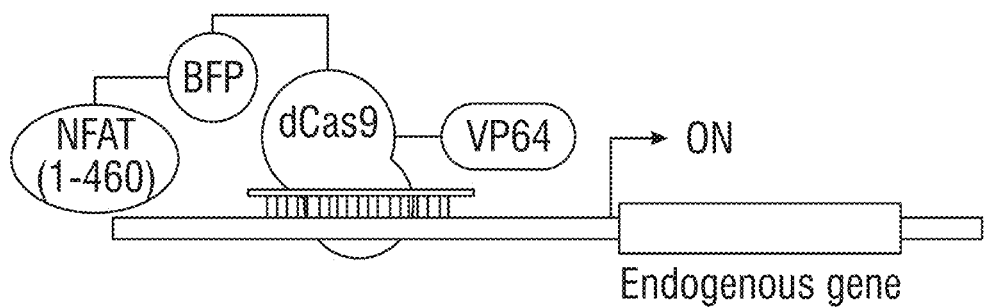
FIG. 7A and FIG. 7B illustrate CaRROT-mediated light-inducible activation of endogenous gene expression. Light-induced endogenous gene expression of MYOD1, FIG. 7A, and ASCL1, FIG. 7B, in HEK293T cells were measured by qRT-PCR. Cells were transfected with dCas9-NLS-VP64 as positive control (PC), BFP-tagged-CaRROT-V5 construct, Opto-CRAC-B10 and indicated sgRNAs or the empty plasmid (pTriEX-BFP). Cells were subjected to pulsed blue light stimulation (470 nm, 50 µW/cm$^2$). *$P<0.05$; *$P<0.001$; **$P<0.0001$ compared to the dark group (two-tailed Student's t-test).
Figure 7A:
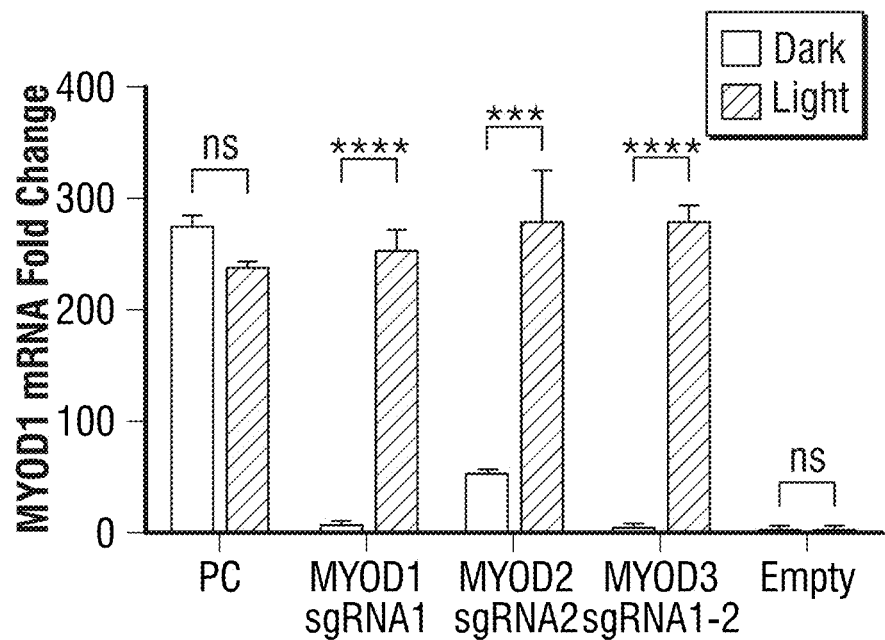
Figure 7B:
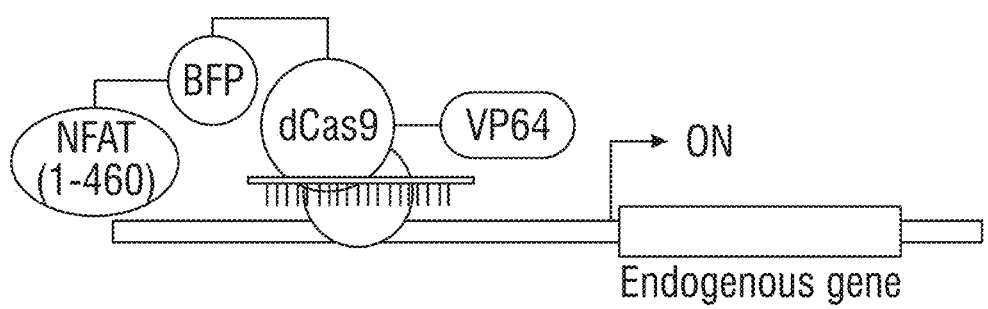
Figure 7B:
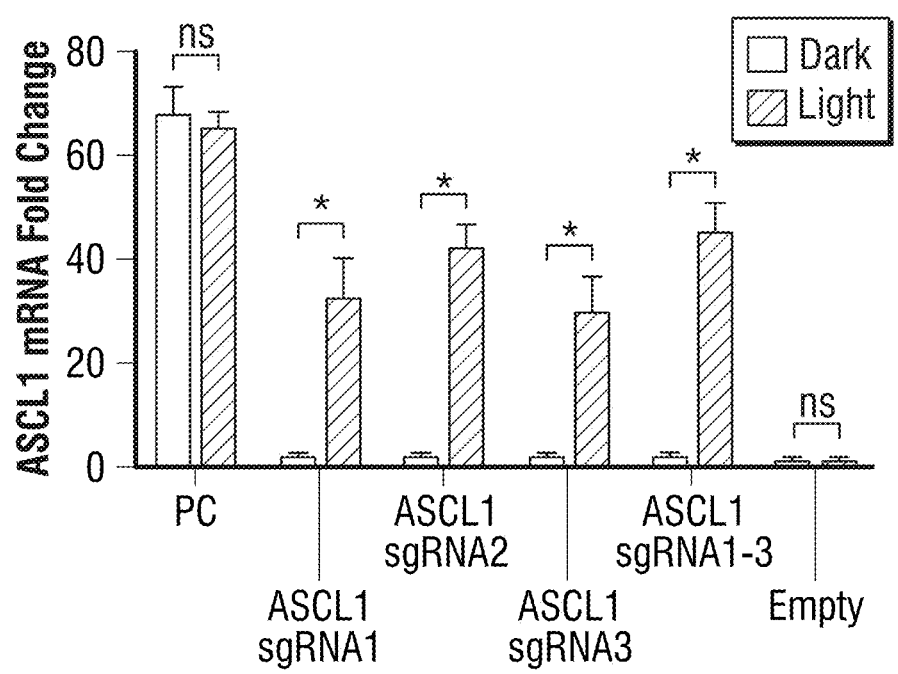

To demonstrate that the synthetic system would also allow photoactivation of endogenous genes, a set of sgRNAs designed to target the promoter regions of the human achaete-scute family bHLH transcription factor 1 (ASCL1) or myogenic differentiation 1 (MYOD1) were used, and then evaluated their light-dependent transcription in HEK293T cells. ASCL1 acts as a pioneer transcription factor to control neuronal differentiation; whereas MYOD1 is a key regulator for skeletal muscle differentiation, which is able to induce transdifferentiation of fibroblasts or other cell types into myocytes. Provided their fundamental roles in developmental biology, light-inducible expression of ASCL1 or MYOD1 will likely be useful for future temporal control of the differentiation of neurons or muscle cells in regenerative medicine. Therefore, these two genes were chosen to test the CaRROT system. Cells transfected with dCas9-NLS-VP64 were used as positive control, which showed the light-independent expression of both genes (left bars, FIG. 7A, FIG. 7B). For cells transfected with CaRROT-V5 and Opto-CRAC-B10, a significant increase in gene expression was observed upon light illumination for each individual or combined sgRNAs. For MYOD1, the mean levels of expression were enhanced by over 200-fold, which was comparable to those of dCas9-NLS-VP64 expressing cells (FIG. 7A). The remarkable light-dependent transcription was also observed when the ASCL1 locus was targeted (FIG. 7B). In all cases, gene expression levels in cells maintained in the dark were comparable to cells transfected with the empty vectors (right bar, FIG. 7A, FIG. 7B). Notably, the coexpression of the system with two sgRNAs targeted MYOD1 or three sgRNAs targeted ASCL1 did not show a significant difference compared to individual sgRNA transfection, suggesting that the expression of multiple guide RNAs targeted to the same gene does not seem to cause synergistic activation of both endogenous genes ASCL1 and MYOD1 (FIG. 7A, 7B). This observation also indicates that by using the system described herein, one well-designed sgRNA probably would be sufficient to activate the expression of endogenous genes.

A synthetic transcriptional reprogramming device (CaRROT) is provided herein that can be tightly controlled by chemicals and/or light to induce endogenous gene transcription with high precision. Since the system relies on the generation of $Ca^{2+}$ signals to drive nuclear translocation of CaRROT, it can be further extended to record or permanently mark $Ca^{2+}$ dependent activities in neurons or lymphocytes once coupled with a reporter gene (e.g., GFP or luciferase).

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially," "approximately," "generally," and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim is an open group. The terms "a," "an," and other singular terms are intended to include the plural forms thereof unless specifically excluded.

What is claimed is:

1. A device for modulating intracellular gene expression, wherein the device comprises a calcium actuator component and a transcription reprogramming component, wherein the calcium actuator component is a near-infrared light (NIR) or blue light-stimulable optogenetic platform which photoactivates ORAI calcium channels located in a cell membrane to induce calcium influx into the cell, and wherein the transcription reprogramming component is a calcium-responsive dCas9 fusion construct comprising an N-terminal fragment (residues $NFAT_{1-460}$) of nuclear factor of activated T-cells (NFAT) fused with dCas9 and a transcriptional coactivator.

2. The device of claim 1, wherein the NIR or blue light-stimulable optogenetic platform comprises an ORAI-activating fragment from a cytoplasmic domain of at least one of STIM1 and LOV2.

3. The device of claim 2, wherein the cytoplasmic domain of STIM1 is at least one of SOAR and CAD.

4. The device of claim 1, wherein the NIR or blue light-stimulable optogenetic platform is LOV2-SOAR.

5. The device of claim 1, wherein the transcriptional coactivator is at least one of VP64 and VP160.

6. The device of claim 1, wherein the calcium-responsive dCas9 fusion construct is $NFAT_{1-460}$-dCas9-VP64.

7. The device of claim 1, wherein the transcription reprogramming component translocates from cytosol to the nucleus when subject to at least one of photoactivation and chemical activation.

8. The device of claim 1, wherein the calcium actuator component has a sequence selected from the group consisting of SEQ ID NO: 1, SEQ ID NO: 2, SEQ ID NO: 6, SEQ ID NO: 7, SEQ ID NO: 8, or SEQ ID NO: 9.

9. The device of claim 1, wherein the transcription reprogramming component has a sequence selected from the group consisting of SEQ ID NO: 3, SEQ ID NO: 4, or SEQ ID NO: 5.

10. The device of claim 1, further comprising a small guide RNA (sgRNA).

11. The device of claim 10, wherein the sgRNA has a sequence selected from the group consisting of SEQ ID NO: 10, SEQ ID NO: 11, or SEQ ID NO: 12.

12. A method for modulating intracellular gene expression, the method comprising:
inducing the device of claim 1 with at least one of light and a chemical;
causing an increase in $Ca^{2+}$; and
translocating the transcription reprogramming component from cytosol to the nucleus.

13. The method of claim 12, wherein the NIR-stimulable optogenetic platform comprises an ORAI-activating fragment from a cytoplasmic domain of at least one of STIM1 and LOV2.

14. The method of claim 13, wherein the cytoplasmic domain of STIM1 is at least one of SOAR and CAD.

15. The method of claim 12, wherein the NIR-stimulable optogenetic platform is LOV2-SOAR.

16. The method of claim 12, wherein the transcriptional coactivator is at least one of VP64 and VP160.

17. The method of claim 12, wherein the calcium-responsive dCas9 fusion construct is $NFAT_{1-460}$-dCas9-VP64.

18. A method for modulating gene intracellular expression, the method comprising:
inducing the device of claim 1 with at least one of light and a chemical, wherein the NIR-stimulable optogenetic platform facilitates $Ca^{2+}$ release, and wherein the NIR-stimulable optogenetic platform is LOV2-SOAR;
causing an increase in $Ca^{2+}$; and
translocating a calcium-responsive dCas9 fusion construct from cytosol to the nucleus, wherein the calcium-responsive dCas9 fusion construct is $NFAT_{1-460}$-dCas9-VP64.

* * * * *

SEQUENCE LISTING

```
<160> NUMBER OF SEQ ID NOS: 12

<210> SEQ ID NO 1
<211> LENGTH: 5746
<212> TYPE: DNA
<213> ORGANISM: Artificial Sequence
<220> FEATURE:
<223> OTHER INFORMATION: dCas9-VP64-mCh-linker-AsLOV2-NLS1

<400> SEQUENCE: 1
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga agaacctgat cggagccctg ctgttcgaca gcggcgaaac agccgaggcc     180
acccggctga gagaaccgc cagaagaaga tacaccagac ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggacg aggtggccta ccacgagaag taccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga accccgacaa cagcgacgtg     540
gacaagctgt tcatccagct ggtgcagacc tacaaccagc tgttcgagga aaacccatc      600 aacgccagcg gcgtggacgc caaggccatc ctgtctgcca gactgagcaa gagcagacgg     660
ctggaaaatc tgatcgccca gctgcccggc gagaagaaga tggcctgtt cggcaacctg     720 attgccctga gcctgggcct gacccccaac ttcaagagca acttcgacct ggccgaggat     780
gccaaactgc agctgagcaa ggacacctac gacgacgacc tggacaacct gctggcccag     840
atcggcgacc agtacgccga cctgtttctg gccgccaaga cctgtccga cgccatcctg     900 ctgagcgaca tcctgagagt gaacaccgag atcaccaagg ccccctgag cgcctctatg     960 atcaagagat acgacgagca ccaccaggac ctgacctgc tgaaagctct cgtgcggcag    1020
cagctgcctg agaagtacaa agagattttc ttcgaccaga gcaagaacgg ctacgccggc    1080
```

```
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga aaagcccgc cttcctgagc   1620 ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctttta agaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc   2280 gaaatggcca gagagaacca gaccacccag aagggacaga agaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggacgccatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact ttttcaagac cgagattacc ctggccaacg gcgagatccg gaagcggcct   3180
ctgatcgaga caaacggcga aaccggggag atcgtgtggg ataagggccg ggattttgcc   3240
accgtgcgga aagtgctgag catgccccaa gtgaatatcg tgaaaaagac cgaggtgcag   3300
acaggcggct tcagcaaaga gtctatcctg cccaagagga acagcgataa gctgatcgcc   3360
agaaagaagg actgggaccc taagaagtac ggcggcttcg acagcccac cgtggcctat   3420
```

```
tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780
cacaagcact acctggacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga cagcgaggcc agcgggccgg ccggatccgg gcgcgccgac    4140
gcgctggacg atttcgatct cgacatgctg ggttctgatg ccctcgatga ctttgacctg    4200
gatatgttgg gaagcgacgc attggatgac tttgatctgg acatgctcgg ctccgatgct    4260
ctggacgatt tcgatctcga tatgttaggg tcagacgcac tggatgattt cgaccttgat    4320
atgttgggaa gcgatgccct tgatgatttc gacctggaca tgctcggcag cgacgccctg    4380
gacgatttcg atctggacat gctggggtcc gatgccttgg atgattttga cttggatatg    4440
ctggggagtg atgccctgga cgactttgac ctggacatgc tgggctccga tgcgctcgat    4500
gacttcgatt tggatatgtt gtatatcgat gtgagcaagg gcgaggagga taacatggcc    4560
atcatcaagg agttcatgcg cttcaaggtg cacatggagg gctccgtgaa cggccacgag    4620
ttcgagatcg agggcgaggg cgagggccgc ccctacgagg gcacccagac cgccaagctg    4680
aaggtgacca agggtggccc cctgcccttc gcctgggaca tcctgtcccc tcagttcatg    4740
tacggctcca aggcctacgt gaagcacccc gccgacatcc ccgactactt gaagctgtcc    4800
ttccccgagg gcttcaagtg ggagcgcgtg atgaacttcg aggacggcgg cgtggtgacc    4860
gtgacccagg actcctccct gcaggacggc gagttcatct acaaggtgaa gctgcgcggc    4920
accaacttcc cctccgacgg ccccgtaatg cagaagaaga ccatgggctg ggaggcctcc    4980
tccgagcgga tgtaccccga ggacggcgcc ctgaagggcg agatcaagca gaggctgaag    5040
ctgaaggacg gcggccacta cgacgctgag gtcaagacca cctacaaggc caagaagccc    5100
gtgcagctgc ccggcgccta caacgtcaac atcaagttgg acatcacctc ccacaacgag    5160
gactacacca tcgtggaaca gtacgaacgc gccgagggcc gccactccac cggcggcatg    5220
gacgagctgt acaagggtgg atctggaggt tcaggtggaa gttttggcta ctacacttga    5280
acgtattgag aagaactttg tcattactga cccaagattg ccagataatc ccattatatt    5340
cgcgtccgat agtttcttgc agttgacaga atatagccgt gaagaaattt gggaagaaa    5400
ctgcaggttt ctacaaggtc ctgaaactga tcgcgcgaca gtgagaaaaa ttagagatgc    5460
catagataac caaacagagg tcactgttca gctgattaat tatacaaaga gtggtaaaaa    5520
gttctggaac ctcttcact tgcagccat gcgagatcag aagggagatg tccagtactt    5580
tattggggtt cagttggatg gaactgagca tgtccgagat gctgccgaga gagggagt     5640
catgctgatt aagaaaactg cagaaaatat tgacgaggcc gcaaagagac tgcccgacgc    5700
caacctggcc gcagcagccg cagccaagaa gaaaaagctg gactag                  5746
```

```
<210> SEQ ID NO 2
<211> LENGTH: 486
<212> TYPE: DNA
<213> ORGANISM: Artificial Sequence
<220> FEATURE:
<223> OTHER INFORMATION: AsLov2-NLS2

<400> SEQUENCE: 2
atgttggcta ctacacttga acgtattgag aagaactttg tcattactga cccaagattg      60
ccagataatc ccattatatt cgcgtccgat agtttcttgc agttgacaga atatagccgt     120
gaagaaattt tgggaagaaa ctgcaggttt ctacaaggtc ctgaaactga tcgcgcgaca     180
gtgagaaaaa ttagagatgc catagataac aaacagagg tcactgttca gctgattaat      240
tatacaaaga gtggtaaaaa gttctggaac ctctttcact gcagcctat gcgagatcag      300 aagggagatg tccagtactt tattgggggtt cagttggatg gaactgagca tgtccgagat    360
gctgccgaga gagggagt catgctgatt aagaaactg cagaaaatat tgacgaggcc        420
gcaaagagac tgcccgacgc caacctggca gccgcagcca agaccaagag aaagaaactg     480
gactag                                                                486

<210> SEQ ID NO 3
<211> LENGTH: 6702
<212> TYPE: DNA
<213> ORGANISM: Artificial Sequence
<220> FEATURE:
<223> OTHER INFORMATION: NLS-dCas9-VP64-mNFAT1(1-460)-GFP

<400> SEQUENCE: 3
atgccgaaga aaaagcgcaa ggtcgaagcg tccgacaaga agtacagcat cggcctggcc       60
atcggcacca actctgtggg ctgggccgtg atcaccgacg agtacaaggt gcccagcaag      120
aaattcaagg tgctgggcaa caccgaccgg cacagcatca gaagaaccct gatcggagcc      180
ctgctgttcg acagcggcga aacagccgag gccaccccgg ctgaagagaac cgccagaaga    240 agatacacca gacggaagaa ccggatctgc tatctgcaag agatcttcag caacgagatg      300
gccaaggtgg acgacagctt cttccacaga ctggaagagt ccttcctggt ggaagaggat      360
aagaagcacg agcggcaccc catcttcggc aacatcgtgg acgaggtggc ctaccacgag     420
aagtacccca ccatctacca cctgagaaag aaactggtgg acagcaccga caaggccgac     480
ctgcggctga tctatctggc cctggcccac atgatcaagt tccggggcca cttcctgatc      540
gagggcgacc tgaaccccga caacagcgac gtggacaagc tgttcatcca gctggtgcag     600
acctacaacc agctgttcga ggaaaacccc atcaacgcca cggcgtgga cgccaaggcc      660 atcctgtctg ccagactgag caagagcaga cggctggaaa atctgatcgc ccagctgccc    720
ggcgagaaga gaatggcct gttcggcaac ctgattgccc tgagcctggg cctgaccccc     780
aacttcaaga gcaacttcga cctggccgag gatgccaaac tgcagctgag caaggacacc     840
tacgacgacg acctggacaa cctgctggcc cagatcggcg accagtacgc cgacctgttt    900
ctggccgcca gaacctgtc cgacgccatc ctgctgagcg acatcctgag agtgaacacc     960
gagatcacca ggccccccct gagcgcctct atgatcaaga gatacgacga gcaccaccag   1020
gacctgaccc tgctgaaagc tctcgtgcgg cagcagctgc tgagaagta caagagatt    1080 ttcttcgacc agagcaagaa cggctacgcc ggctacattg acggcggagc cagccaggaa   1140
gagttctaca gttcatcaa gcccatcctg gaaaagatgg acggcaccga ggaactgctc    1200
gtgaagctga acagagagga cctgctgcgg aagcagcgga ccttcgacaa cggcagcatc   1260
```

```
ccccaccaga tccacctggg agagctgcac gccattctgc ggcggcagga agatttttac    1320
ccattcctga aggacaaccg ggaaaagatc gagaagatcc tgaccttccg catccctac     1380
tacgtgggcc tctggccag gggaaacagc agattcgcct ggatgaccag aaagagcgag    1440
gaaaccatca cccctggaa cttcgaggaa gtggtggaca agggcgcttc cgcccagagc    1500
ttcatcgagc ggatgaccaa cttcgataag aacctgccca cgagaaggt gctgcccaag    1560
cacagcctgc tgtacgagta cttcaccgtg tataacgagc tgaccaaagt gaaatacgtg   1620
accgagggaa tgagaaagcc cgccttcctg agcggcgagc agaaaaaggc catcgtggac   1680
ctgctgttca agaccaaccg gaaagtgacc gtgaagcagc tgaaagagga ctacttcaag   1740
aaaatcgagt gcttcgactc cgtggaaatc tccggcgtgg aagatcggtt caacgcctcc   1800
ctgggcacat accacgatct gctgaaaatt atcaaggaca aggacttcct ggacaatgag   1860
gaaaacgagg acattctgga agatatcgtg ctgaccctga cactgtttga ggacagagag   1920
atgatcgagg aacggctgaa aacctatgcc cacctgttcg acgacaaagt gatgaagcag   1980
ctgaagcggc ggagatacac cggctggggc aggctgagcc ggaagctgat caacggcatc   2040
cgggacaagc agtccggcaa gacaatcctg gatttcctga agtccgacgg cttcgccaac   2100
agaaacttca tgcagctgat ccacgacgac agcctgacct ttaaagagga catccagaaa   2160
gcccaggtgt ccggccaggg cgatagcctg cacgagcaca ttgccaatct ggccggcagc   2220
cccgccatta gaagggcat cctgcagaca gtgaaggtgg tggacgagct cgtgaaagtg   2280
atgggccggc acaagcccga gaacatcgtg atcgaaatgg ccagagagaa ccagaccacc   2340
cagaagggac agaagaacag ccgcgagaga atgaagcgga tcgaagaggg catcaaagag   2400
ctgggcagcc agatcctgaa agaacacccc gtggaaaaca cccagctgca gaacgagaag   2460
ctgtacctgt actacctgca gaatgggcgg gatatgtacg tggaccagga actggacatc   2520
aaccggctgt ccgactacga tgtggacgcc atcgtgcctc agagctttct gaaggacgac   2580
tccatcgaca caaggtgct gaccagaagc gacaagaacc ggggcaagag cgacaacgtg   2640
ccctccgaag aggtcgtgaa gaagatgaag aactactggc ggcagctgct gaacgccaag   2700
ctgattaccc agagaaagtt cgacaatctg accaaggccg agaggcgg cctgagcgaa   2760
ctggataagg ccggcttcat caagagacag ctggtggaaa cccggcagat cacaaagcac   2820
gtggcacaga tcctggactc ccggatgaac actaagtacg acgagaatga caagctgatc   2880
cgggaagtga aagtgatcac cctgaagtcc aagctggtgt ccgatttccg gaaggatttc   2940
cagttttaca aagtgcgcga gatcaacaac taccaccacg cccacgacgc ctacctgaac   3000
gccgtcgtgg gaaccgccct gatcaaaaag taccctaagc tggaaagcga gttcgtgtac   3060
ggcgactaca aggtgtacga cgtgcggaag atgatcgcca gagcgagca ggaaatcggc   3120
aaggctaccg ccaagtactt cttctacagc aacatcatga cttttttcaa gaccgagatt   3180
accctggcca acggcgagat ccggaagcgg cctctgatcg agacaaacgg cgaaaccggg   3240
gagatcgtgt gggataaggg ccgggatttt gccaccgtgc ggaaagtgct gagcatgccc   3300
caagtgaata tcgtgaaaaa gaccgaggtg cagacaggcg gcttcagcaa agagtctatc   3360
ctgcccaaga ggaacagcga taagctgatc gccagaaaga aggactggga ccctaagaag   3420
tacggcggct tcgacagccc caccgtggcc tattctgtgc tggtggtggc caaagtggaa   3480
aagggcaagt ccaagaaact gaagagtgtg aaagagctgc tggggatcac catcatggaa   3540
agaagcagct tcgagaagaa tcccatcgac tttctggaag ccaagggcta caaagaagtg   3600
aaaaaggacc tgatcatcaa gctgcctaag tactccctgt tcgagctgga aaacggccgg   3660
```

```
aagagaatgc tggcctctgc cggcgaactg cagaagggaa acgaactggc cctgccctcc   3720
aaatatgtga acttcctgta cctggccagc cactatgaga agctgaaggg ctcccccgag   3780
gataatgagc agaaacagct gtttgtggaa cagcacaagc actacctgga cgagatcatc   3840
gagcagatca gcgagttctc caagagagtg atcctggccg acgctaatct ggacaaagtg   3900
ctgtccgcct acaacaagca ccgggataag cccatcagag agcaggccga atatcatc    3960 cacctgttta ccctgaccaa tctgggagcc cctgccgcct tcaagtactt tgacaccacc   4020
atcgaccgga gaggtacac cagcaccaaa gaggtgctgg acgccaccct gatccaccag   4080
agcatcaccg gcctgtacga gacacggatc gacctgtctc agctgggagg cgacagcccc   4140
aagaagaaga gaaaggtgga ggccagcggg ccggccggat ccgggcgcgc cgacgcgctg   4200
gacgatttcg atctcgacat gctgggttct gatgccctcg atgactttga cctggatatg   4260
ttgggaagcg acgcattgga tgactttgat ctggacatgc tcggctccga tgctctggac   4320
gatttcgatc tcgatatgtt agggtcgac gcactggatg atttcgacct tgatatgttg   4380
ggaagcgatg cccttgatga tttcgacctg acatgctcg gcagcgacgc cctggacgat   4440
ttcgatctgg acatgctggg gtccgatgcc ttgatgatt ttgacttgga tatgctgggg   4500
agtgatgccc tggacgactt tgacctggac atgctgggct ccgatgcgct cgatgacttc   4560
gatttggata tgttgtatat cgatatgccg gagccgcagc ccgaccccga tggcggggac   4620
ggccccggcc acgagcccgg gggcagtccc caagacgagc tggacttttc catcctcttc   4680
gattatgact atctgaaccc tatcgaagaa gaaccgatcg cacataaggc catcagctca   4740
ccctccggac tcgcataccc ggatgatgtc ctggactatg gcctcaagcc atgcaacccc   4800
cttgccagtc cctctggcga gcccctggcc cggttcggag agccggatag tatagggttc   4860
cagaactttc tgagcccggt caagccagca ggggcttcgg gcccgagccc tcggatcgag   4920
atcactccat cccacgaact gatgcaggca ggggggggccc tccgtgggag agacgccggc   4980
ctgtcccccg agcagccggc cctggccctg gccggcgtgg ccgccagccc gaggttcaca   5040
ctgcccgtgc ccggctacga gggctaccgc gagccgcttt gcttgagccc cgctagcagc   5100
ggctcctctg ccagcttcat ttctgacacc ttctcccccct acacctcgcc ctgcgtctca   5160
cccaataacg ccgggcccga cgacctgtgt ccccagtttc aaaacatccc tgctcattat   5220
tcccccagaa cctctccaat aatgtcacct cgaaccagcc tcgccgagga cagctgcctg   5280
ggccgacact cgcccgtgcc ccgtccggca tcccgctcct cctcacccgg tgccaagcgg   5340
aggcattcgt gcgcagaggc tttggttgct cctctgcccg cagcctcacc ccagcgctcc   5400
cggagcccct cgccacagcc ctcgcctcac gtggcaccgc aggacgacag catccccgct   5460 gggtacccccc ccacgccgg ctctgctgtt ctcatggatg ccctcaacac cctggccacc   5520
gactcgccct gcgggatccc ctccaagata tggaagacca gtcctgaccc gacgcctgtg   5580
tccaccgctc cgtccaaggc tggcctgcc cgccacatct accctactgt ggagttcctg   5640
gggccatgtg agcaggagga gaggaggaat tccgctccag agtccatcct gctggtacca   5700
cctacttggc ccaagcagtt ggtgccggcc attcccatct gcagcatccc tgtgactgca   5760
tccctcccac cactcgagtg gccactctcc aatcagtcgg gctcctatga gctacggatt   5820
gaggtccaac ccaagcccca tcaccggggcc cactatgaga cggagggcag ccgtggcgct   5880
gtcaaagccc caacaggagg acaccctgtg gtgcagctcc acggctacat ggagaacaag   5940
cctctggggc ttcagatcca gatcgatcca ccggtcgcca ccatggtgag caagggcgag   6000
```

| | |
|---|---|
| gagctgttca ccggggtggt gcccatcctg gtcgagctgg acggcgacgt aaacggccac | 6060 |
| aagttcagcg tgtccggcga gggcgagggc gatgccacct acggcaagct gaccctgaag | 6120 |
| ttcatctgca ccaccggcaa gctgcccgtg cctggcccca ccctcgtgac caccctgacc | 6180 |
| tacggcgtgc agtgcttcag ccgctacccc gaccacatga gcagcacga cttcttcaag | 6240 |
| tccgccatgc ccgaaggcta cgtccaggag cgcaccatct tcttcaagga cgacggcaac | 6300 |
| tacaagaccc gcgccgaggt gaagttcgag ggcgacaccc tggtgaaccg catcgagctg | 6360 |
| aagggcatcg acttcaagga ggacggcaac atcctggggc acaagctgga gtacaactac | 6420 |
| aacagccaca acgtctatat catggccgac aagcagaaga acggcatcaa ggtgaacttc | 6480 |
| aagatccgcc acaacatcga ggacggcagc gtgcagctcg ccgaccacta ccagcagaac | 6540 |
| acccccatcg gcgacggccc cgtgctgctg cccgacaacc actacctgag cacccagtcc | 6600 |
| gccctgagca agacccccaa cgagaagcgc gatcacatgg tcctgctgga gttcgtgacc | 6660 |
| gccgccggga tcactctcgg catggacgag ctgtacaagt aa | 6702 |

<210> SEQ ID NO 4
<211> LENGTH: 6747
<212> TYPE: DNA
<213> ORGANISM: Artificial Sequence
<220> FEATURE:
<223> OTHER INFORMATION: mNFAT1(1-460)-GFP-HA-NLS-dCas9-NLS-VP64

<400> SEQUENCE: 4

| | |
|---|---|
| atgccggagc cgcagcccga ccccgatggc ggggacggcc ccggccacga gcccggggc | 60 |
| agtccccaag acgagctgga cttttccatc ctcttcgatt atgactatct gaaccctatc | 120 |
| gaagaagaac cgatcgcaca taaggccatc agctcaccct ccggactcgc atacccggat | 180 |
| gatgtcctgg actatggcct caagccatgc aaccccttg ccagtccctc tggcgagccc | 240 |
| cctggccggt tcggagagcc ggatagtata gggttccaga actttctgag cccggtcaag | 300 |
| ccagcagggg cttcgggccc gagccctcgg atcgagatca ctccatccca cgaactgatg | 360 |
| caggcagggg gggccctccg tgggagagac gccggcctgt cccccgagca gccggccctg | 420 |
| gccctggccg cgctggccgc cagcccgagg ttcacactgc ccgtgcccgg ctacgagggc | 480 |
| taccgcgagc cgctttgctt gagccccgct agcagcggct cctctgccag cttcatttct | 540 |
| gacaccttct cccctacac ctcgccctgc gtctcaccca ataacgccgg gcccgacgac | 600 |
| ctgtgtcccc agtttcaaaa catccctgct cattattccc ccagaacctc tccaataatg | 660 |
| tcacctcgaa ccagcctcgc cgaggacagc tgcctgggcc gacactcgcc cgtgcccgt | 720 |
| ccggcatccc gctcctcctc acccggtgcc aagcggaggc attcgtgcgc agaggctttg | 780 |
| gttgctcctc tgcccgcagc ctcacccag cgctcccgga gccccctcgcc acagccctcg | 840 |
| cctcacgtgg caccgcagga cgacagcatc cccgctgggt acccccccac ggccggctct | 900 |
| gctgttctca tggatgccct caacaccctg gccaccgact cgccctgcgg gatcccctcc | 960 |
| aagatatgga gaccagtcc tgacccgacg cctgtgtcca ccgctccgtc caaggctggc | 1020 |
| ctggcccgcc acatctaccc tactgtggag ttcctggggc catgtgagca ggaggagagg | 1080 |
| aggaattccg ctccagagtc catcctgctg gtaccaccta cttggcccaa gcagttggtg | 1140 |
| ccggccattc ccatctgcag catccctgtg actgcatccc tccaccact cgagtggcca | 1200 |
| ctctccaatc agtcgggctc ctatgagcta cggattgagg tccaacccaa gccccatcac | 1260 |
| cgggcccact atgagacgga gggcagccgt ggcgctgtca agcccccaac aggaggacac | 1320 |
| cctgtggtgc agctccacgg ctacatggag aacaagcctc tggggcttca gatccagatc | 1380 |

```
gatccaccgg tcgccaccat ggtgagcaag ggcgaggagc tgttcaccgg ggtggtgccc    1440
atcctggtcg agctggacgg cgacgtaaac ggccacaagt tcagcgtgtc cggcgagggc    1500
gagggcgatg ccacctacgg caagctgacc ctgaagttca tctgcaccac cggcaagctg    1560
cccgtgccct ggcccaccct cgtgaccacc ctgacctacg gcgtgcagtg cttcagccgc    1620
taccccgacc acatgaagca gcacgacttc ttcaagtccg ccatgcccga aggctacgtc    1680
caggagcgca ccatcttctt caaggacgac ggcaactaca agacccgcgc cgaggtgaag    1740
ttcgagggcg acaccctggt gaaccgcatc gagctgaagg gcatcgactt caaggaggac    1800
ggcaacatcc tggggcacaa gctggagtac aactacaaca gccacaacgt ctatatcatg    1860
gccgacaagc agaagaacgg catcaaggtg aacttcaaga tccgccacaa catcgaggac    1920
ggcagcgtgc agctcgccga ccactaccag cagaacaccc ccatcggcga cggccccgtg    1980
ctgctgcccg acaaccacta cctgagcacc cagtccgccc tgagcaaaga ccccaacgag    2040
aagcgcgatc acatggtcct gctggagttc gtgaccgccg ccgggatcac tctcggcatg    2100
gacgagctgt acaagggcag cggtaagctt atgtacccat acgatgttcc agattacgct    2160
tcgccgaaga aaaagcgcaa ggtcgaagcg tccgacaaga agtacagcat cggcctggcc    2220
atcggcacca actctgtggg ctgggccgtg atcaccgacg agtacaaggt gcccagcaag    2280
aaattcaagg tgctgggcaa caccgaccgg cacagcatca agaagaacct gatcggagcc    2340
ctgctgttcg acagcggcga aacagccgag gccacccggc tgaagagaac cgccagaaga    2400
agatacacca gacggaagaa ccggatctgc tatctgcaag agatcttcag caacgagatg    2460
gccaaggtgg acgacagctt cttccacaga ctggaagagt ccttcctggt ggaagaggat    2520
aagaagcacg agcggcaccc catcttcggc aacatcgtgg acgaggtggc ctaccacgag    2580
aagtacccca ccatctacca cctgagaaag aaactggtgg acagcaccga caaggccgac    2640
ctgcggctga tctatctggc cctggcccac atgatcaagt tccggggcca cttcctgatc    2700
gagggcgacc tgaaccccga caacagcgac gtggacaagc tgttcatcca gctggtgcag    2760
acctacaacc agctgttcga ggaaaacccc atcaacgcca gcggcgtgga cgccaaggcc    2820
atcctgtctg ccagactgag caagagcaga cggctggaaa atctgatcgc ccagctgccc    2880
ggcgagaaga gaatggcct gttcggcaac ctgattgccc tgagcctggg cctgacccc    2940 aacttcaaga gcaacttcga cctggccgag gatgccaaac tgcagctgag caaggacacc    3000
tacgacgacg acctggacaa cctgctggcc cagatcggcg accagtacgc cgacctgttt    3060
ctggccgcca gaacctgtc cgacgccatc ctgctgagcg acatcctgag agtgaacacc    3120
gagatcacca aggcccccct gagcgcctct atgatcaaga gatacgacga gcaccaccag    3180
gacctgaccc tgctgaaagc tctcgtgcgg cagcagctgc ctgagaagta caaagagatt    3240
ttcttcgacc agagcaagaa cggctacgcc ggctacattg acggcggagc cagccaggaa    3300
gagttctaca agttcatcaa gcccatcctg gaaaagatgg acggcaccga ggaactgctc    3360
gtgaagctga acagagagga cctgctgcgg aagcagcgga ccttcgacaa cggcagcatc    3420
ccccaccaga tccacctggg agagctgcac gccattctgc ggcggcagga agatttttac    3480
ccattcctga aggacaaccg ggaaaagatc gagaagatcc tgaccttccg catccctac    3540 tacgtgggcc ctctggccag gggaaacagc agattcgcct ggatgaccag aaagagcgag    3600
gaaaccatca cccctggaa cttcgaggaa gtggtggaca agggcgcttc cgcccagagc    3660
ttcatcgagc ggatgaccaa cttcgataag aacctgccca acgagaaggt gctgcccaag    3720
```

```
cacagcctgc tgtacgagta cttcaccgtg tataacgagc tgaccaaagt gaaatacgtg    3780
accgagggaa tgagaaagcc cgccttcctg agcggcgagc agaaaaaggc catcgtggac    3840
ctgctgttca agaccaaccg gaaagtgacc gtgaagcagc tgaaagagga ctacttcaag    3900
aaaatcgagt gcttcgactc cgtggaaatc tccggcgtgg aagatcggtt caacgcctcc    3960
ctgggcacat accacgatct gctgaaaatt atcaaggaca aggacttcct ggacaatgag    4020
gaaaacgagg acattctgga agatatcgtg ctgacccctg cactgtttga ggacagagag    4080
atgatcgagg aacggctgaa aacctatgcc cacctgttcg acgacaaagt gatgaagcag    4140
ctgaagcggc ggagatacac cggctggggc aggctgagcc ggaagctgat caacggcatc    4200
cgggacaagc agtccggcaa gacaatcctg gatttcctga gtccgacggg cttcgccaac    4260
agaaacttca tgcagctgat ccacgacgac agcctgacct ttaaagagga catccagaaa    4320
gcccaggtgt ccggccaggg cgatagcctg cacgagcaca ttgccaatct ggccggcagc    4380
cccgccatta gaagggcat cctgcagaca gtgaaggtgg tggacgagct cgtgaaagtg    4440
atgggccggc acaagcccga aaacatcgtg atcgaaatgg ccagagagaa ccagaccacc    4500
cagaagggac agaagaacag ccgcgagaga atgaagcgga tcgaagaggg catcaaagag    4560
ctgggcagcc agatcctgaa agaacacccc gtggaaaaca cccagctgca gaacgagaag    4620
ctgtacctgt actacctgca gaatgggcgg gatatgtacg tggaccagga actggacatc    4680
aaccggctgt ccgactacga tgtggacgcc atcgtgcctc agagctttct gaaggacgac    4740
tccatcgaca caaggtgct gaccagaagc gacaagaacc ggggcaagag cgacaacgtg    4800
ccctccgaag aggtcgtgaa gaagatgaag aactactggc ggcagctgct gaacgccaag    4860
ctgattaccc agagaaagtt cgacaatctg accaaggccg agagaggcgg cctgagcgaa    4920
ctggataagg ccggcttcat caagagacag ctggtggaaa cccggcagat cacaaagcac    4980
gtggcacaga tcctggactc ccggatgaac actaagtacg acgagaatga caagctgatc    5040
cgggaagtga aagtgatcac cctgaagtcc aagctggtgt ccgatttccg gaaggatttc    5100
cagttttaca aagtgcgcga gatcaacaac taccaccacg cccacgacgc ctacctgaac    5160
gccgtcgtgg aaccgccct gatcaaaaag taccctaagc tggaaagcga gttcgtgtac    5220
ggcgactaca aggtgtacga cgtgcggaag atgatcgcca agagcgagca ggaaatcggc    5280
aaggctaccg ccaagtactt cttctacagc aacatcatga actttttcaa gaccgagatt    5340
accctggcca acggcgagat ccggaagcgg cctctgatcg agacaaacgg cgaaaccggg    5400
gagatcgtgt gggataaggg ccgggatttt gccaccgtgc ggaaagtgct gagcatgccc    5460
caagtgaata tcgtgaaaaa gaccgaggtg cagacaggcg gcttcagcaa agagtctatc    5520
ctgcccaaga ggaacagcga taagctgatc gccagaaaga aggactggga ccctaagaag    5580
tacggcggct tcgacagccc caccgtggcc tattctgtgc tggtggtggc caaagtggaa    5640
aagggcaagt ccaagaaact gaagagtgtg aaagagctgc tggggatcac catcatggaa    5700
agaagcagct tcgagaagaa tcccatcgac tttctggaag ccaagggcta caaagaagtg    5760
aaaaaggacc tgatcatcaa gctgcctaag tactccctgt tcgagctgga aaacggccgg    5820
aagagaatgc tggcctctgc cggcgaactg cagaagggaa acgaactggc cctgccctcc    5880
aaatatgtga acttcctgta cctggccagc cactatgaga agctgaaggg ctcccccgag    5940
gataatgagc agaaacagct gtttgtggaa cagcacaagc actacctgga cgagatcatc    6000
gagcagatca gcgagttctc caagagagtg atcctggccg acgctaatct ggacaaagtg    6060
ctgtccgcct acaacaagca ccgggataag cccatcagag agcaggccga gaatatcatc    6120
```

| | |
|---|---|
| cacctgttta ccctgaccaa tctgggagcc cctgccgcct tcaagtactt tgacaccacc | 6180 |
| atcgaccgga agaggtacac cagcaccaaa gaggtgctgg acgccaccct gatccaccag | 6240 |
| agcatcaccg gcctgtacga gacacggatc gacctgtctc agctgggagg cgacagcccc | 6300 |
| aagaagaaga gaaaggtgga ggccagcggg ccggccggat ccgggcgcgc cgacgcgctg | 6360 |
| gacgatttcg atctcgacat gctgggttct gatgccctcg atgactttga cctggatatg | 6420 |
| ttgggaagcg acgcattgga tgactttgat ctggacatgc tcggctccga tgctctggac | 6480 |
| gatttcgatc tcgatatgtt agggtcagac gcactggatg atttcgacct tgatatgttg | 6540 |
| ggaagcgatg cccttgatga tttcgacctg gacatgctcg gcagcgacgc cctggacgat | 6600 |
| ttcgatctgg acatgctggg gtccgatgcc ttggatgatt ttgacttgga tatgctgggg | 6660 |
| agtgatgccc tggacgactt tgacctggac atgctgggct ccgatgcgct cgatgacttc | 6720 |
| gatttggata tgttgtatat cgattaa | 6747 |

<210> SEQ ID NO 5
<211> LENGTH: 6705
<212> TYPE: DNA
<213> ORGANISM: Artificial Sequence
<220> FEATURE:
<223> OTHER INFORMATION: mNFAT1(1-460)-GFP-HA-dCas9-VP64

<400> SEQUENCE: 5

| | |
|---|---|
| atgccggagc cgcagcccga ccccgatggc ggggacggcc ccggccacga gcccggggc | 60 |
| agtccccaag acgagctgga cttttccatc ctcttcgatt atgactatct gaaccctatc | 120 |
| gaagaagaac cgatcgcaca taaggccatc agctcaccct ccggactcgc atacccggat | 180 |
| gatgtcctgg actatggcct caagccatgc aaccccttg ccagtccctc tggcgagccc | 240 |
| cctggccggt tcggagagcc ggatagtata gggttccaga actttctgag cccggtcaag | 300 |
| ccagcagggg cttcgggccc gagccctcgg atcgagatca ctccatccca cgaactgatg | 360 |
| caggcagggg gggccctccg tgggagagac gccggcctgt ccccgagca gccggccctg | 420 |
| gccctggccg gcgtggccgc cagcccgagg ttcacactgc ccgtgccgg ctacgagggc | 480 |
| taccgcgagc cgctttgctt gagccccgct agcagcggct cctctgccag cttcatttct | 540 |
| gacaccttct cccctacac ctcgccctgc gtctcaccca taacgccgg gccgacgac | 600 |
| ctgtgtcccc agtttcaaaa catccctgct cattattccc ccagaacctc tccaataatg | 660 |
| tcacctcgaa ccagcctcgc cgaggacagc tgcctgggcc gacactcgcc cgtgcccgt | 720 |
| ccggcatccc gctcctcctc acccggtgcc aagcggagc attcgtgcgc agaggctttg | 780 |
| gttgctcctc tgcccgcagc ctcaccccag cgctcccgga gccctcgcc acagccctcg | 840 |
| cctcacgtgg caccgcagga cgacagcatc ccgctgggt acccccac ggccggctct | 900 |
| gctgttctca tggatgccct caacaccctg gccaccgact cgccctgcgg gatcccctcc | 960 |
| aagatatgga agaccagtcc tgacccgacg cctgtgtcca ccgctccgtc caaggctggc | 1020 |
| ctggcccgcc acatctaccc tactgtggag ttcctgggc catgtgagca ggaggagagg | 1080 |
| aggaattccg ctccagagtc catcctgctg gtaccaccta cttggcccaa gcagttggtg | 1140 |
| ccggccattc ccatctgcag catccctgtg actgcatccc tcccaccact cgagtggcca | 1200 |
| ctctccaatc agtcgggctc ctatgagcta cggattgagg tccaacccaa gccccatcac | 1260 |
| cgggcccact atgagacgga gggcagccgt ggcgctgtca aagccccaac aggaggacac | 1320 |
| cctgtggtgc agctccacgg ctacatggag aacaagcctc tggggcttca gatccagatc | 1380 |

```
gatccaccgg tcgccaccat ggtgagcaag ggcgaggagc tgttcaccgg ggtggtgccc      1440
atcctggtcg agctggacgg cgacgtaaac ggccacaagt tcagcgtgtc cggcgagggc      1500
gagggcgatg ccacctacgg caagctgacc ctgaagttca tctgcaccac cggcaagctg      1560
cccgtgccct ggcccaccct cgtgaccacc ctgacctacg gcgtgcagtg cttcagccgc      1620
taccccgacc acatgaagca gcacgacttc ttcaagtccg ccatgcccga aggctacgtc      1680
caggagcgca ccatcttctt caaggacgac ggcaactaca agacccgcgc cgaggtgaag      1740
ttcgagggcg acaccctggt gaaccgcatc gagctgaagg gcatcgactt caaggaggac      1800
ggcaacatcc tggggcacaa gctggagtac aactacaaca gccacaacgt ctatatcatg      1860
gccgacaagc agaagaacgg catcaaggtg aacttcaaga tccgccacaa catcgaggac      1920
ggcagcgtgc agctcgccga ccactaccag cagaacaccc ccatcggcga cggccccgtg      1980
ctgctgcccg acaaccacta cctgagcacc cagtccgccc tgagcaaaga ccccaacgag      2040
aagcgcgatc acatggtcct gctggagttc gtgaccgccg ccgggatcac tctcggcatg      2100
gacgagctgt acaagggcag cggtaagctt atgtacccat acgatgttcc agattacgct      2160
tcggaagcgt ccgacaagaa gtacagcatc ggcctggcca tcggcaccaa ctctgtgggc      2220
tgggccgtga tcaccgacga gtacaaggtg cccagcaaga aattcaaggt gctgggcaac      2280
accgaccggc acagcatcaa gaagaacctg atcggagccc tgctgttcga cagcggcgaa      2340
acagccgagg ccacccggct gaagagaacc gccagaagaa gatacaccag acggaagaac      2400
cggatctgct atctgcaaga gatcttcagc aacgagatgg ccaaggtgga cgacagcttc      2460
ttccacagac tggaagagtc cttcctggtg gaagaggata agaagcacga gcggcacccc      2520
atcttcggca acatcgtgga cgaggtggcc taccacgaga gtaccccac catctaccac      2580
ctgagaaaga aactggtgga cagcaccgac aaggccgacc tgcggctgat ctatctggcc      2640
ctggcccaca tgatcaagtt ccggggccac ttcctgatcg agggcgacct gaaccccgac      2700
aacagcgacg tggacaagct gttcatccag ctggtgcaga cctacaacca gctgttcgag      2760
gaaaacccca tcaacgccag cggcgtggac gccaaggcca tcctgtctgc cagactgagc      2820
aagagcagac ggctggaaaa tctgatcgcc cagctgcccg gcgagaagaa gaatggcctg      2880
ttcggcaacc tgattgccct gagcctgggc ctgaccccca acttcaagag caacttcgac      2940
ctggccgaga tgccaaaact gcagctgagc aaggacacct acgacgacga cctggacaac      3000
ctgctggccc agatcggcga ccagtacgcc gacctgtttc tggccgccaa gaacctgtcc      3060
gacgccatcc tgctgagcga catcctgaga gtgaacaccg agatcaccaa ggcccccctg      3120
agcgcctcta tgatcaagag atacgacgag caccaccagg acctgaccct gctgaaagct      3180
ctcgtgcggc agcagctgcc tgagaagtac aaagagattt tcttcgacca gagcaagaac      3240
ggctacgccg gctacattga cggcggagcc agccaggaag agttctacaa gttcatcaag      3300
cccatcctgg aaaagatgga cggcaccgag gaactgctcg tgaagctgaa cagagaggac      3360
ctgctgcgga agcagcggac cttcgacaac ggcagcatcc ccaccagat ccacctggga      3420
gagctgcacg ccattctgcg gcggcaggaa gatttttacc cattcctgaa ggacaaccgg      3480
gaaaagatcg agaagatcct gaccttccgc atccccact acgtgggccc tctggccagg      3540
ggaaacagca gattcgcctg gatgaccaga aagagcgagg aaaccatcac ccctggaac      3600
ttcgaggaag tggtggacaa gggcgcttcc gcccagagct tcatcgagcg gatgaccaac      3660
ttcgataaga acctgcccaa cgagaaggtg ctgcccaagc acagcctgct gtacgagtac      3720
ttcaccgtgt ataacgagct gaccaaagtg aaatacgtga ccgagggaat gagaaagccc      3780
```

-continued

```
gccttcctga gcggcgagca gaaaaaggcc atcgtggacc tgctgttcaa gaccaaccgg   3840
aaagtgaccg tgaagcagct gaaagaggac tacttcaaga aaatcgagtg cttcgactcc   3900
gtggaaatct ccggcgtgga agatcggttc aacgcctccc tgggcacata ccacgatctg   3960
ctgaaaatta tcaaggacaa ggacttcctg acaatgagg aaaacgagga cattctggaa    4020
gatatcgtgc tgaccctgac actgtttgag acagagaga tgatcgagga acggctgaaa   4080
acctatgccc acctgttcga cgacaaagtg atgaagcagc tgaagcggcg agatacacc    4140
ggctggggca ggctgagccg gaagctgatc aacggcatcc gggacaagca gtccggcaag   4200
acaatcctgg atttcctgaa gtccgacggc ttcgccaaca gaaacttcat gcagctgatc   4260
cacgacgaca gcctgacctt taaagaggac atccagaaag cccaggtgtc cggccagggc   4320
gatagcctgc acgagcacat tgccaatctg gccggcagcc ccgccattaa gaagggcatc   4380
ctgcagacag tgaaggtggt ggacgagctc gtgaaagtga tgggccggca aagcccgag    4440
aacatcgtga tcgaaatggc cagagagaac cagaccaccc agaagggaca gaagaacagc   4500
cgcgagagaa tgaagcggat cgaagagggc atcaaagagc tgggcagcca gatcctgaaa   4560
gaacaccccg tggaaaacac ccagctgcag aacgagaagc tgtacctgta ctacctgcag   4620
aatgggcggg atatgtacgt ggaccaggaa ctggacatca accggctgtc cgactacgat   4680
gtggacgcca tcgtgcctca gagctttctg aaggacgact ccatcgacaa caaggtgctg   4740
accagaagcg acaagaaccg gggcaagagc gacaacgtgc cctccgaaga ggtcgtgaag   4800
aagatgaaga actactggcg gcagctgctg aacgccaagc tgattaccca gagaaagttc   4860
gacaatctga ccaaggccga gagaggcggc ctgagcgaac tggataaggc cggcttcatc   4920
aagagacagc tggtggaaac ccggcagatc acaaagcacg tggcacagat cctggactcc   4980
cggatgaaca ctaagtacga cgagaatgac aagctgatcc gggaagtgaa agtgatcacc   5040
ctgaagtcca gctggtgtc cgatttccgg aaggatttcc agttttacaa agtgcgcgag    5100
atcaacaact accaccacgc ccacgacgcc tacctgaacg ccgtcgtggg aaccgccctg   5160
atcaaaaagt acccctaagct ggaaagcgag ttcgtgtacg cgactacaa ggtgtacgac    5220
gtgcggaaga tgatcgccaa gagcgagcag gaaatcggca aggctaccgc caagtacttc   5280
ttctacagca acatcatgaa cttttttcaag accgagatta ccctggccaa cggcgagatc   5340
cggaagcggc ctctgatcga gacaaacggc gaaaccgggg agatcgtgtg ggataagggc   5400
cgggattttg ccaccgtgcg gaaagtgctg agcatgcccc aagtgaatat cgtgaaaaag   5460
accgaggtgc agacaggcgg cttcagcaaa gagtctatcc tgcccaagag gaacagcgat   5520
aagctgatcg ccagaaagaa ggactgggac cctaagaagt acggcggctt cgacagcccc   5580
accgtggcct attctgtgct ggtggtggcc aaagtggaaa agggcaagtc caagaaactg   5640
aagagtgtga agagctgctg ggggatcacc atcatggaaa gagcagctt cgagaagaat   5700
cccatcgact ttctggaagc caagggctac aaagaagtga aaaaggacct gatcatcaag   5760
ctgcctaagt actccctgtt cgagctggaa aacggccgga gagaatgct ggcctctgcc    5820
ggcgaactgc agaagggaaa cgaactggcc ctgccctcca aatatgtgaa cttcctgtac   5880
ctggccagcc actatgagaa gctgaagggc tcccccgagg ataatgagca gaaacagctg   5940
tttgtggaac agcacaagca ctacctggac gagatcatcg agcagatcag cgagttctcc   6000
aagagagtga tcctggccga cgctaatctg gacaaagtgc tgtccgccta caacaagcac   6060
cgggataagc ccatcagaga gcaggccgag aatatcatcc acctgtttac cctgaccaat   6120
```

| | |
|---|---|
| ctgggagccc ctgccgcctt caagtacttt gacaccacca tcgaccggaa gaggtacacc | 6180 |
| agcaccaaag aggtgctgga cgccaccctg atccaccaga gcatcaccgg cctgtacgag | 6240 |
| acacggatcg acctgtctca gctgggaggc gacagcgagg ccagcgggcc ggccggatcc | 6300 |
| gggcgcgccg acgcgctgga cgatttcgat ctcgacatgc tgggttctga tgccctcgat | 6360 |
| gactttgacc tggatatgtt gggaagcgac gcattggatg actttgatct ggacatgctc | 6420 |
| ggctccgatg ctctggacga tttcgatctc gatatgttag gtcagacgc actggatgat | 6480 |
| ttcgaccttg atatgttggg aagcgatgcc cttgatgatt tcgacctgga catgctcggc | 6540 |
| agcgacgccc tggacgattt cgatctggac atgctggggt ccgatgcctt ggatgatttt | 6600 |
| gacttggata tgctggggag tgatgccctg gacgactttg acctggacat gctgggctcc | 6660 |
| gatgcgctcg atgacttcga tttggatatg ttgtatatcg attaa | 6705 |

<210> SEQ ID NO 6
<211> LENGTH: 891
<212> TYPE: DNA
<213> ORGANISM: Artificial Sequence
<220> FEATURE:
<223> OTHER INFORMATION: LOV2-STIM1 (336-486)
<220> FEATURE:
<221> NAME/KEY: misc_feature
<222> LOCATION: (867)..(867)
<223> OTHER INFORMATION: n is a, c, g, t or u

<400> SEQUENCE: 6

| | |
|---|---|
| ttggctacta cacttgaacg tattgagaag aactttgtca ttactgaccc aagattgcca | 60 |
| gataatccca ttatattcgc gtccgatagt ttcttgcagt tgacagaata tagccgtgaa | 120 |
| gaaattttgg gaagaaactg caggtttcta caaggtcctg aaactgatcg cgcgacagtg | 180 |
| agaaaaatta gagatgccat agataaccaa acagaggtca ctgttcagct gattaattat | 240 |
| acaaagagtg gtaaaaagtt ctggaacctc tttcacttgc agcctatgcg agatcagaag | 300 |
| ggagatgtcc agtactttat tggggttcag ttggatggaa ctgagcatgt ccagatgct | 360 |
| gccgagagag agggagtcat gctgattaag aaaactgcag aaaatattga tgaggcggca | 420 |
| aaagaactta gcttgaatc acacagctca tggtatgctc ctgaggccct gcagaagtgg | 480 |
| ctgcagctga cccatgaggt ggaggtgcag tactacaaca tcaagaagca aatgcagag | 540 |
| aggcagctgc tggtggccaa ggagggggct gagaaaataa aaagaagag aacacgctt | 600 |
| tttggtacct tccatgtggc ccacagctct tccctggatg atgtggatca taaaatccta | 660 |
| actgctaagc aagctctgag tgaggtgaca gcggcactga gggagcgcct gcaccggtgg | 720 |
| cagcagatcg agatcctctg cggttttccag attgtcaata ccccggcat ccactccttg | 780 |
| gtggctgctc tcaacatcga ccccagctgg atgggcagca cccgccctaa ccccgcccac | 840 |
| ttcatcatga ctgacgatgt ggatganatg gatgaggaga ttgtgtcgta a | 891 |

<210> SEQ ID NO 7
<211> LENGTH: 327
<212> TYPE: DNA
<213> ORGANISM: Artificial Sequence
<220> FEATURE:
<223> OTHER INFORMATION: STIM1 (336-442)

<400> SEQUENCE: 7

| | |
|---|---|
| atggaatcac acagctcatg gtatgctcct gaggccctgc agaagtggct gcagctgacc | 60 |
| catgaggtgg aggtgcagta ctacaacatc aagaagcaaa atgcagagag gcagctgctg | 120 |
| gtggccaagg agggggctga gaaataaaa aagaagagaa acacgctttt tggtaccttc | 180 |

```
catgtggccc acagctcttc cctggatgat gtggatcata aaatcctaac tgctaagcaa    240
gctctgagtg aggtgacagc ggcactgagg gagcgcctgc accggtggca gcagatcgag    300
atcctctgcg gtttccagat tgtctaa                                        327
```

```
<210> SEQ ID NO 8
<211> LENGTH: 312
<212> TYPE: DNA
<213> ORGANISM: Artificial Sequence
<220> FEATURE:
<223> OTHER INFORMATION: DrSTIM1 (341-442)

<400> SEQUENCE: 8
atgcttcaaa agtggctgca gctgacacac gaggttgaag tccagtatta caacatcaag    60
aaacagaacg cggaacggca gctgcaagtg gccaaagagg cgccgagaa gatcaaaaag    120 aaacgaaata cactgttcgg gactttccac gttgctcatt cctcctctct ggacgacgtg    180
gatcacaaga ttctggccgc caagcaggct ctcggagagg tgacagcagc cttgagggaa    240
agactgcatc gctggcagca gatcgaactg ctgacgggct ttaccctggt ccataatccc    300
ggtctcccat aa                                                        312
```

```
<210> SEQ ID NO 9
<211> LENGTH: 303
<212> TYPE: DNA
<213> ORGANISM: Artificial Sequence
<220> FEATURE:
<223> OTHER INFORMATION: STIM1 (347-448)

<400> SEQUENCE: 9
gccctgcaga agtggctgca gctgacccat gaggtggagg tgcagtacta caacatcaag    60
aagcaaaatg cagagaggca gctgctggtg gccaaggagg gggctgagaa aataaaaaag    120
aagagaaaca cgcttttggg taccttccat gtggcccaca gctcttccct ggatgatgtg    180
gatcataaaa tcctaactgc taagcaagct ctgagtgagg tgacagcggc actgagggag    240
cgcctgcacc ggtggcagca gatcgagatc ctctgcggtt tccagattgt caataacccc    300
ggc                                                                  303
```

```
<210> SEQ ID NO 10
<211> LENGTH: 20
<212> TYPE: DNA
<213> ORGANISM: Artificial Sequence
<220> FEATURE:
<223> OTHER INFORMATION: ASCL1-sgRNA1

<400> SEQUENCE: 10
cgggagaaag gaacgggagg                                                20
```

```
<210> SEQ ID NO 11
<211> LENGTH: 20
<212> TYPE: DNA
<213> ORGANISM: Artificial Sequence
<220> FEATURE:
<223> OTHER INFORMATION: ASCL1-sgRNA2

<400> SEQUENCE: 11
tccaatttct agggtcaccg                                                20
```

```
<210> SEQ ID NO 12
<211> LENGTH: 20
<212> TYPE: DNA
```

```
<213> ORGANISM: Artificial Sequence
<220> FEATURE:
<223> OTHER INFORMATION: ASCL1-sgRNA3

<400> SEQUENCE: 12
aagaacttga agcaaagcgc                                          20
```